(12) United States Patent
Zhang et al.

(10) Patent No.: US 7,947,501 B2
(45) Date of Patent: May 24, 2011

(54) GENE RECOMBINATION EXCHANGE SYSTEM FOR STABLE GENE MODIFICATION IN HUMAN ES CELLS

(75) Inventors: Su-Chun Zhang, Middleton, WI (US); Zhong-wei Du, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 71 days.

(21) Appl. No.: 12/322,809

(22) Filed: Feb. 6, 2009

(65) Prior Publication Data

US 2009/0239305 A1  Sep. 24, 2009

Related U.S. Application Data

(60) Provisional application No. 61/063,939, filed on Feb. 7, 2008.

(51) Int. Cl.
*C12N 15/87* (2006.01)

(52) U.S. Cl. .............. 435/462; 435/455; 435/463

(58) Field of Classification Search ............... None
See application file for complete search history.

(56) References Cited

U.S. PATENT DOCUMENTS

| | | |
|---|---|---|
| 2006/0014262 A1 | 1/2006 | Endo et al. |
| 2006/0014264 A1 | 1/2006 | Sauer et al. |
| 2006/0128018 A1 | 6/2006 | Zwaka et al. |

OTHER PUBLICATIONS

Adams et al. Molecular Brain Research, 2003, vol. 110, pp. 221-233.*
Zwaka et al. Nature Biotechnology, 2003, vol. 21, pp. 319-321.*
Hockemeyer et al., Nature Biotechnology, 27:9, 851-857 (2009).
Di Domenico et al. Cloning and Stem Cells, 10:2, 217-229 (2008).
Yan et al., Stem Cells, 23, 781-790 (2005).
Vallier et al., Stem Cells, 25, 1490-1497 (2007).
Tan and Droge, Stem Cells, 23, 868-873 (2005).
Yang et al. Stem Cells published online Oct. 18, 2007; doi:10.1634/stemcells.2007-0494.
Girod et al., Nature Methods, 4:9, 747-753 (2007).
Giudice and Trounson, Cell Stem Cell 2, 422-433, May (2008).
Araki et al., J. Biochem., 140:6, 793-798 (2006).
Feng et al., J. Mol. Biol.,292, 779-758 (1999).
Irion et al., Nature Biotechnology, 25:12, 1477-1482 (2007).
Nolden et al., Nature Methods, 3:6, 461-467 (2006).
Cre-Lox recombination, Wikipedia; http://en.wikipedia.org/wiki/cre-lox_recombination, Apr. 10, 2007.

* cited by examiner

*Primary Examiner* — Deborah Crouch
(74) *Attorney, Agent, or Firm* — Quarles & Brady, LLP

(57) ABSTRACT

A method of creating a human pluripotent transgenic stem cell, wherein heterologous DNA is inserted into specific "hotspots" in the genome where stable and high gene expression may occur, is disclosed. In one embodiment, the method comprises the steps of: (a) selecting a pluripotent stem cell line, and (b) inserting heterologous DNA at an insertion site selected from the group consisting of insertion site one and insertion site two to form a transgenic cell line. In another embodiment, the heterologous DNA is an exchange cassette and the transgenic cell line formed is a master cell line.

25 Claims, 17 Drawing Sheets
(16 of 17 Drawing Sheet(s) Filed in Color)

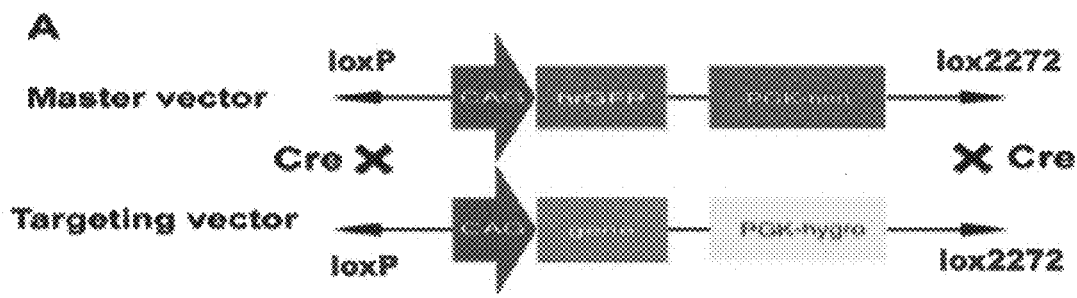
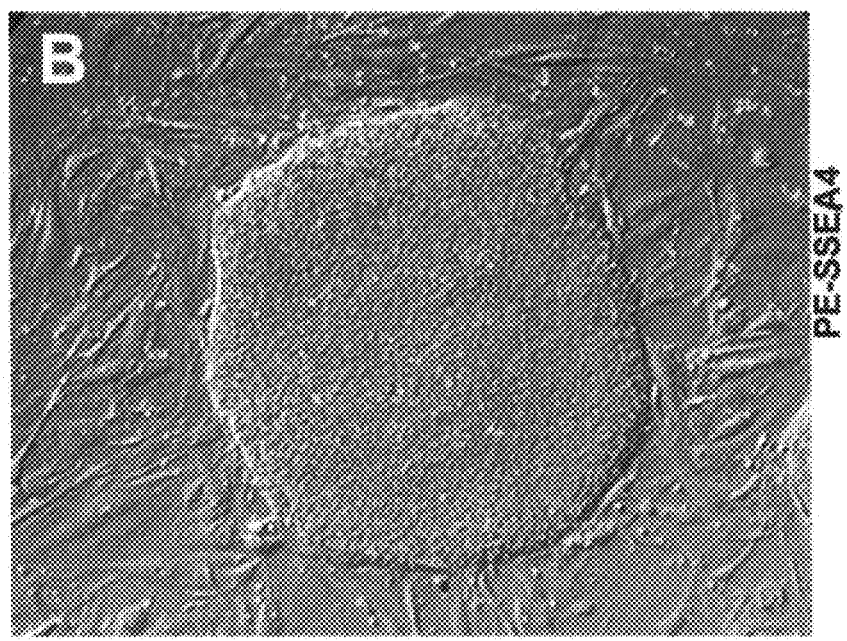
FIG. 1A-B

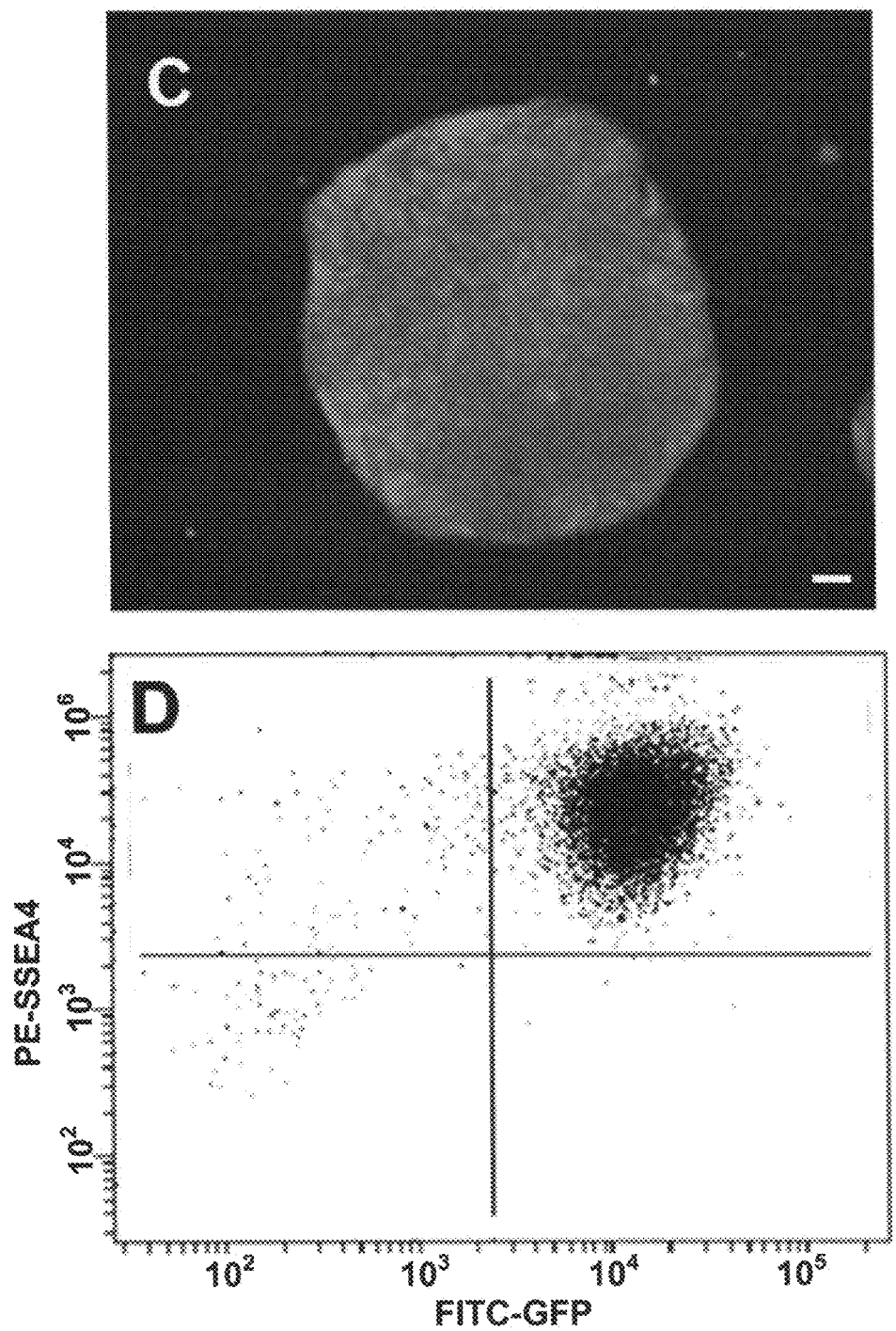
FIG. 1C-D

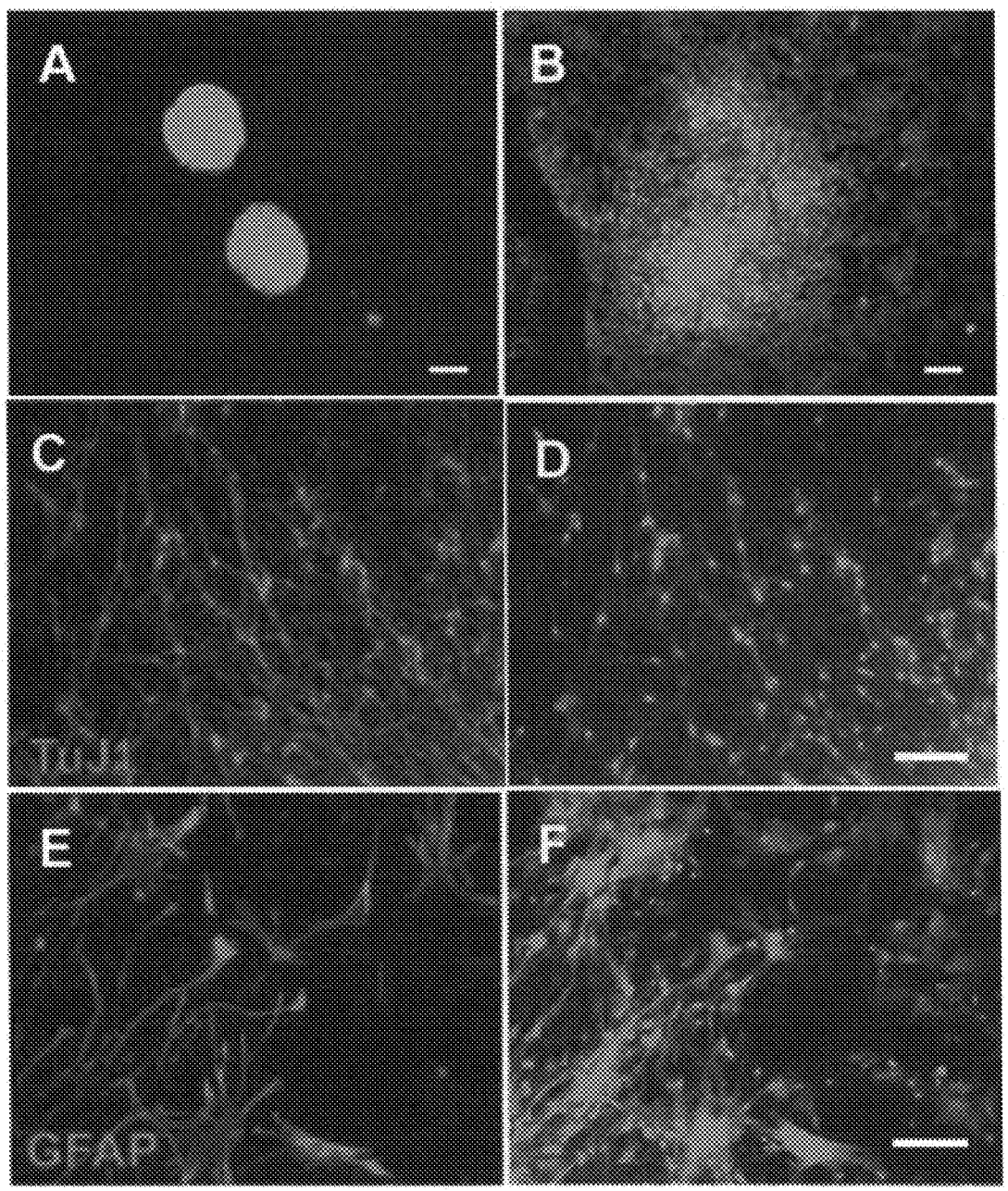
FIG. 2A-F

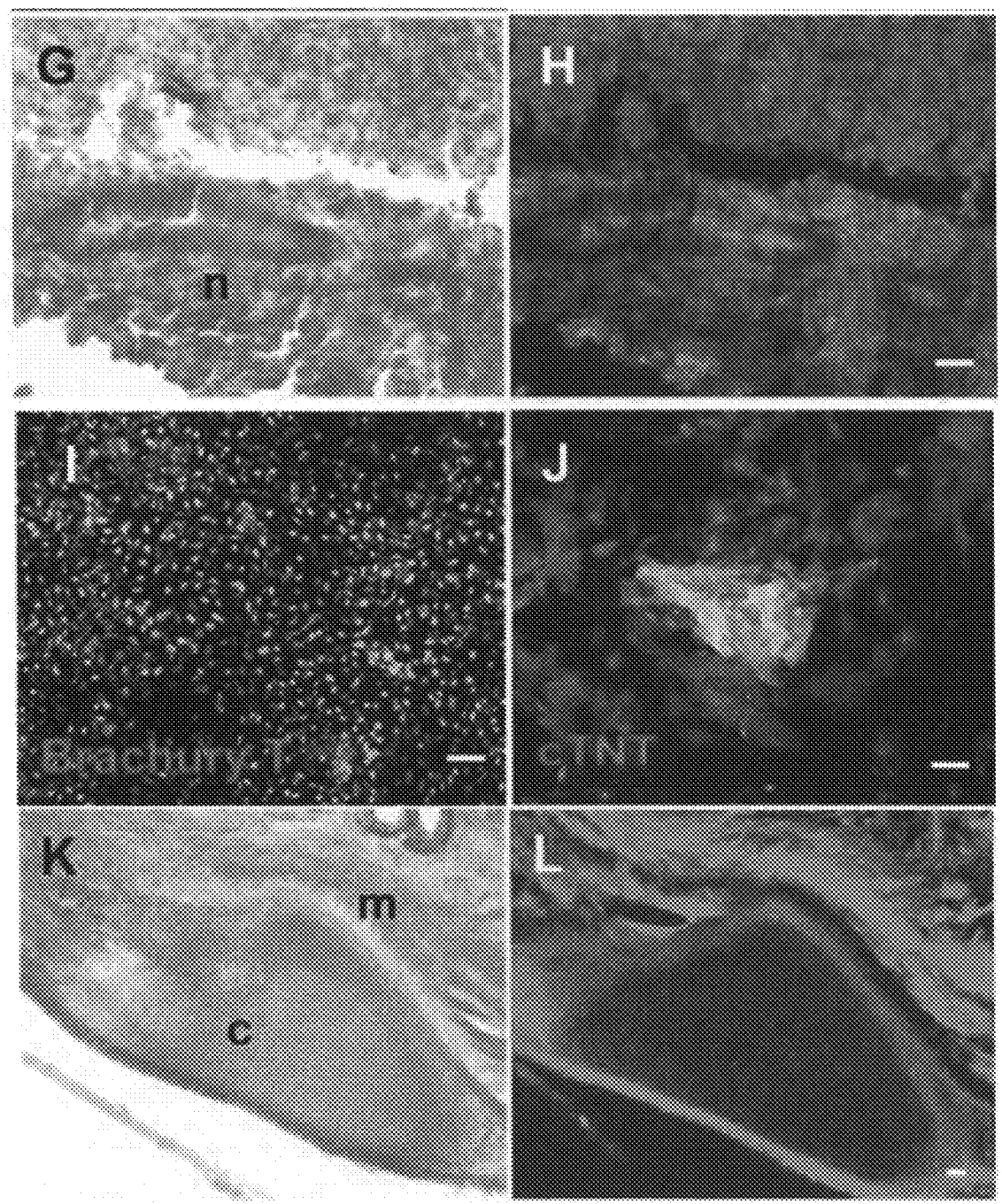
FIG. 2G-L

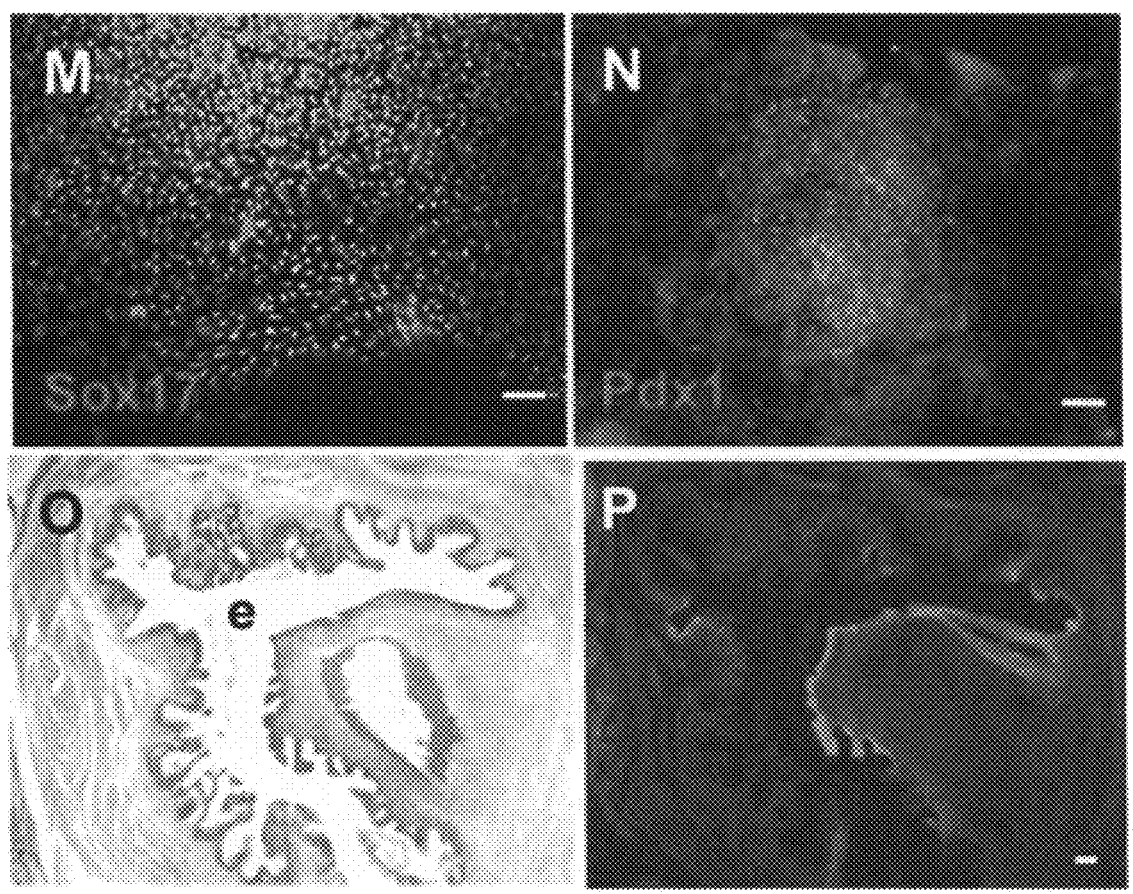
FIG. 2M-P

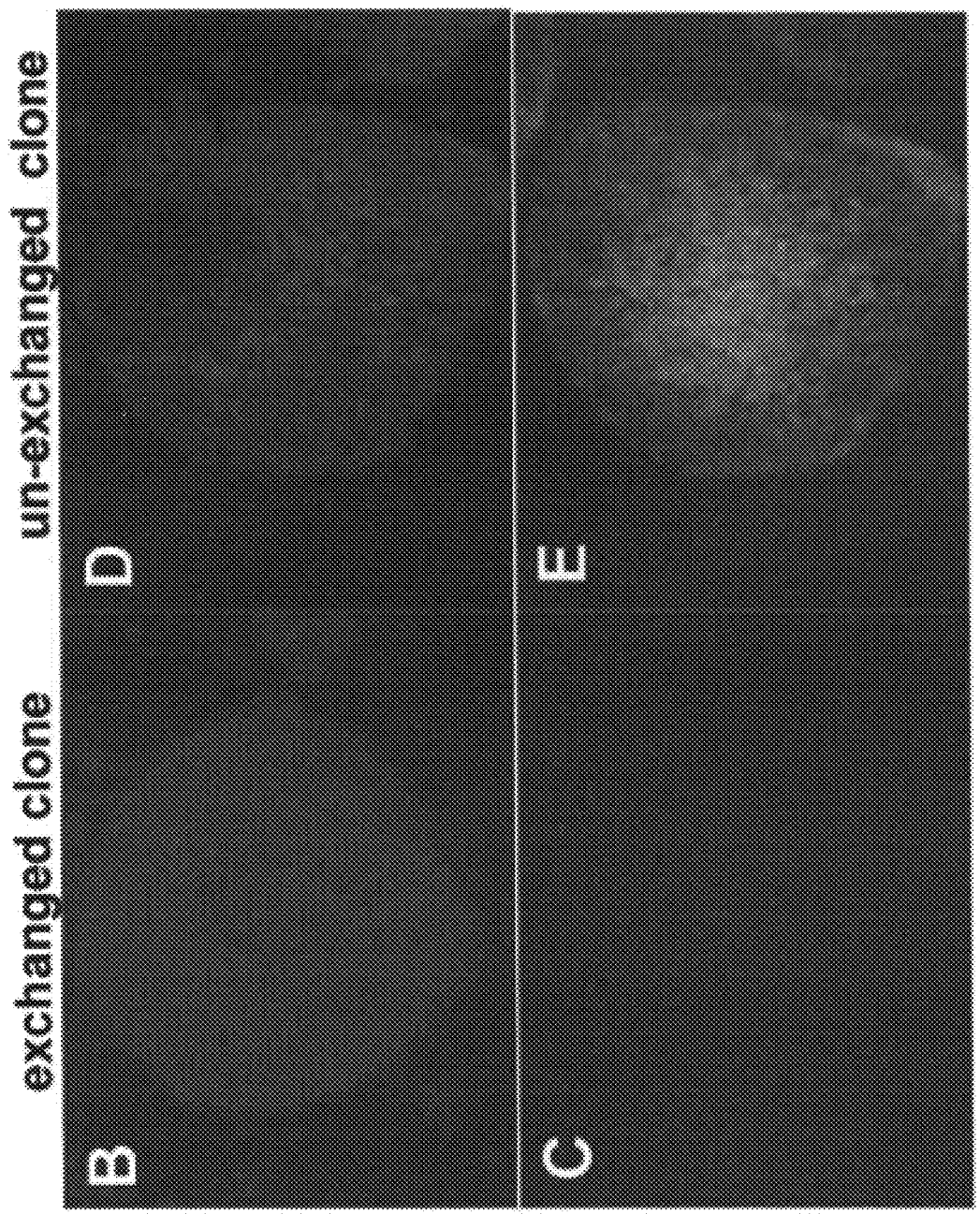
FIG. 3B-E

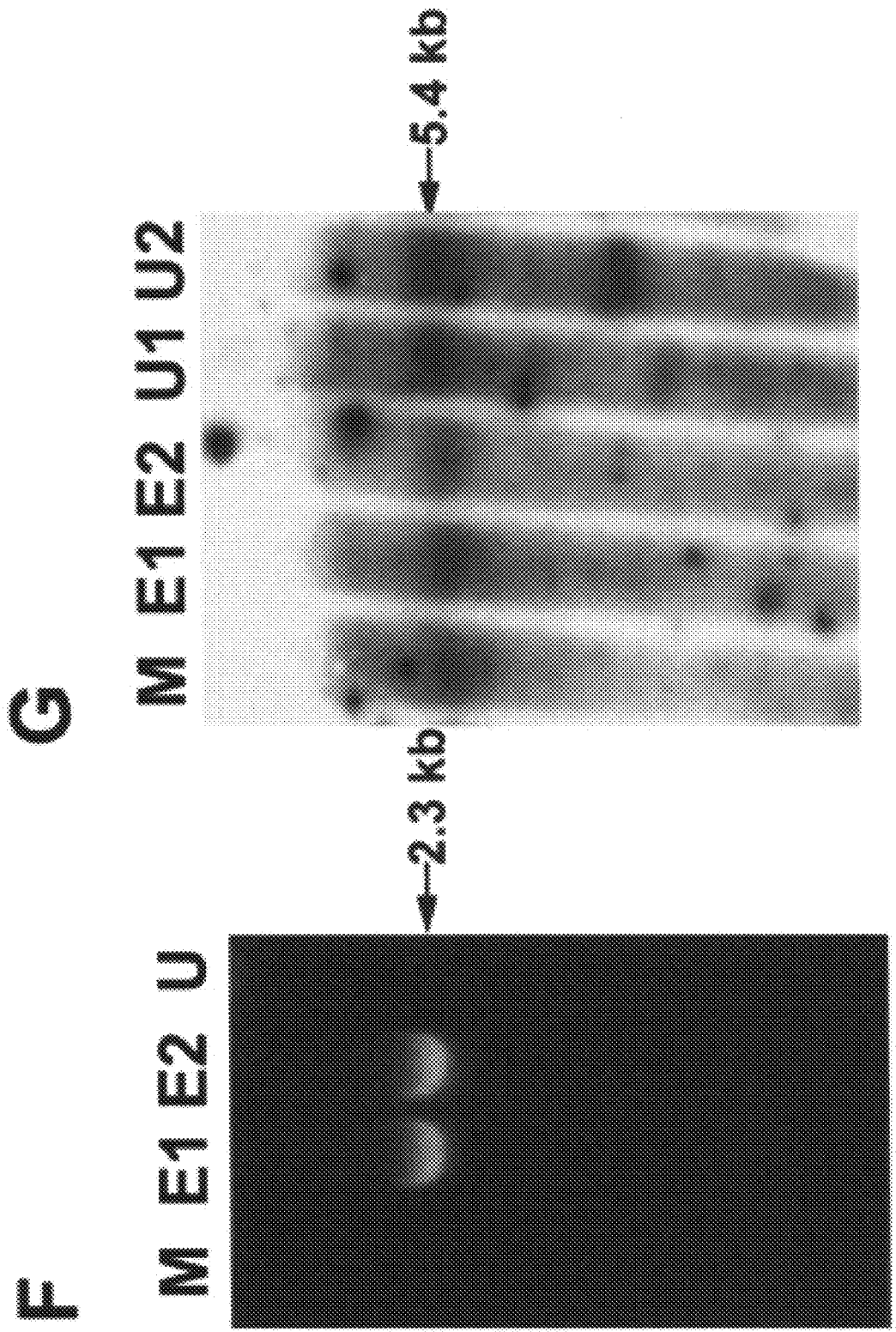
FIG. 3F-G

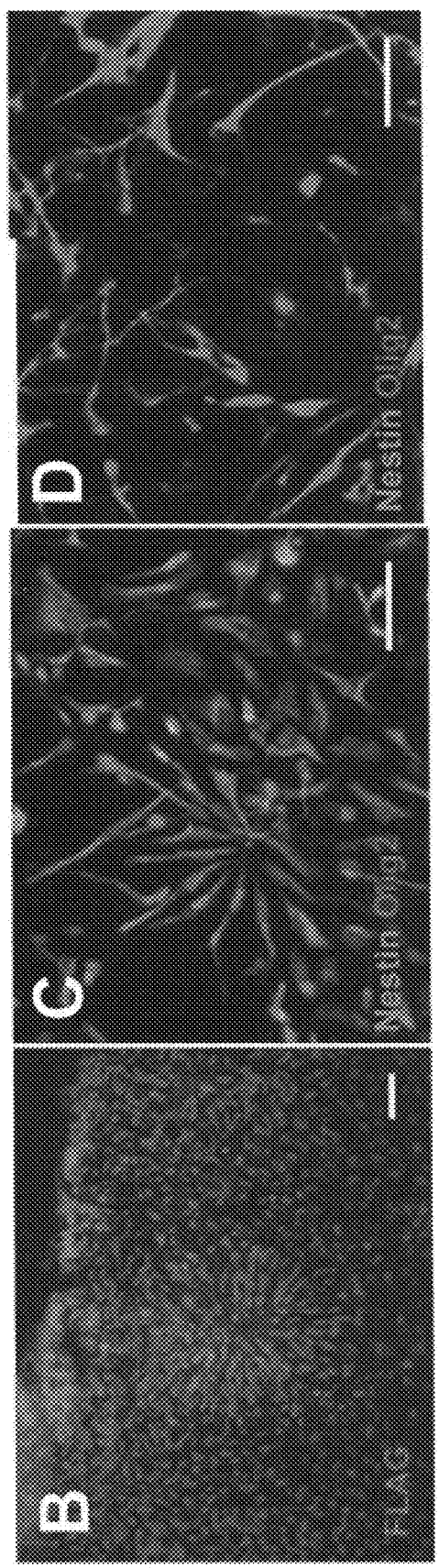
FIG. 4B-D

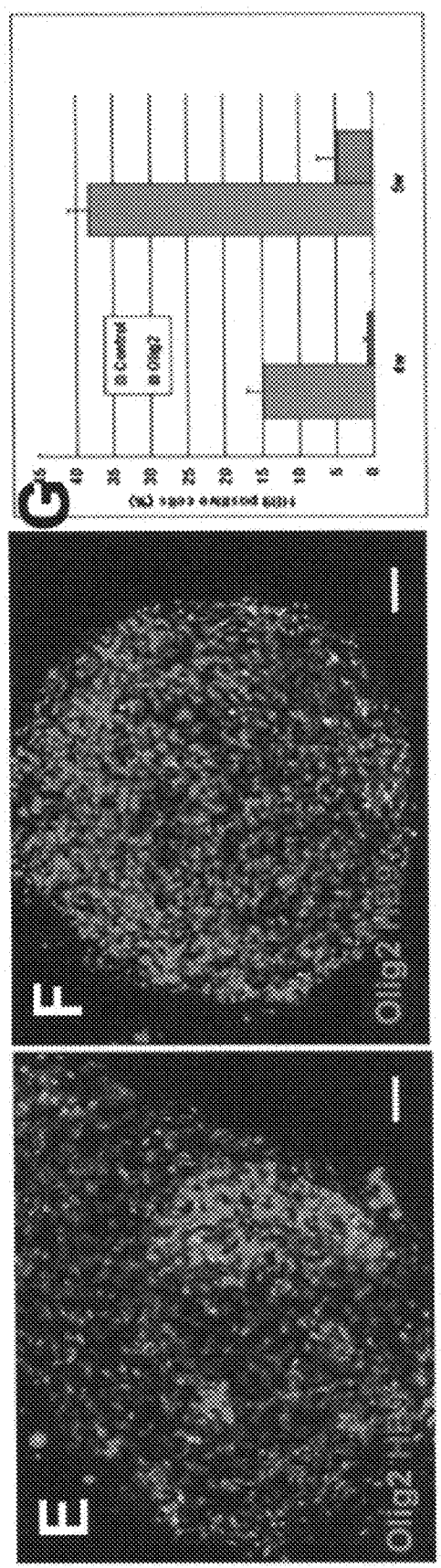
FIG. 4E-G

SEQUENCE LISTING

<160> NUMBER OF SEQ ID NOS: 11

<210> SEQ ID NO 1
<211> LENGTH: 40
<212> TYPE: DNA
<213> ORGANISM: Homo sapiens

<400> SEQUENCE: 1
tgcaatctcc gcctccggac tcaggtgatt ctcccacctc          40

```
<210> SEQ ID NO 2
<211> LENGTH: 40
<212> TYPE: DNA
<213> ORGANISM: Homo sapiens

<400> SEQUENCE: 2
acataggcat gattgattgc atcactggcc aatggcaatc                           40

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 3
cggctctgct tcccttagac t                                              21

<210> SEQ ID NO 4
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 4
tcacagccaa gcattctaca aac                                            23

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
aacgtgtcag tggtggacct g                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonulceotide

<400> SEQUENCE: 6
agtgggtgtc gctgttgaag t                                              21

<210> SEQ ID NO 7
<211> LENGTH: 61
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (52)..(57)
<223> OTHER INFORMATION: n is a, c, g, or t

<400> SEQUENCE: 7
cacgacacgc tactcaacac accacctcgc acagcgtcat caagcggccg cnnnnnngcc    60
t                                                                   61

<210> SEQ ID NO 8
<211> LENGTH: 20
<212> TYPE: DNA
<213> ORGANISM: Artificial Sequence
```

```
<220> FEATURE:
<223> OTHER INFORMATION: Synthetic oligonucleotide

<400> SEQUENCE: 8
cacgacacgc tactcaacac                                              20

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
tatcccgtat tgacgccggg caag                                         24

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 10
actcaacaca ccacctcgca cagc                                         24

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 11
aagagcaact cggtcgccgc atac                                         24
```

GENE RECOMBINATION EXCHANGE SYSTEM FOR STABLE GENE MODIFICATION IN HUMAN ES CELLS

CROSS-REFERENCE TO RELATED APPLICATION

This application claims the benefit of U.S. patent application Ser. No. 61/063,939, filed on Feb. 7, 2008, which is incorporated herein by reference in its entirety.

STATEMENT OF FEDERALLY SPONSORED RESEARCH OR DEVELOPMENT

This invention was made with United States government support awarded by the following agencies: NIH NS045926. The United States government has certain rights in this invention.

BACKGROUND

Human embryonic stem cells (hESCs) offer an invaluable tool for revealing human biology and a potential source of functional cells/tissues for regenerative medicine (Thomson J A et al. Science 1998; 282:1145-1147; Reubinoff B E et al. Nat. Biotechnol. 2000; 18:399-404). Like their mouse counterparts which revolutionize biomedical research through transgenesis for the past decades (Downing G J et al. Stem Cells 2004; 22:1168-1180; Rossant J et al. Philos Trans R Soc Lond B Biol Sci. 1993; 339:207-215), the utility of hESCs including the potential medical application, will likely be significantly enhanced and broadened by our ability to build versatile genetically modified hESC lines (Xia X et al. Biotechnology & Genetic Engineering Reviews 2007; 24:297-310; Zeng X et al. Curr Opin Mol. Ther. 2008; 10:207-213).

Building stable transgenic hESC lines remains a challenging and laborious process. The chief reasons include low transfection and cloning efficiency (Eiges R et al. Curr Biol. 2001; 11:514-518; Zwaka T P et al. Nat. Biotechnol. 2003; 21:319-321) as well as high incidence of transgene silencing caused by the integration site and following cellular differentiation (Liew C G et al. Stem Cells 2007; 25:1521-1528; Xia X et al. Stem Cells Dev. 2007; 16:167-176). At present, lentivirus mediated approach can achieve as high as 40-70% transfection efficiency in hESCs (Xiong C et al. Stem Cells Dev. 2005; 14:367-377; Zhou B Y et al. Stem Cells 2007; 25:779-789). However, its preference of integrating into the gene coding region, which poses a risk of insertional mutagenesis (Schroder A R et al. Cell 2002; 110:521-529; Mitchell R S et al. PLoS Biol. 2004; 2:E234), and the limitation of inserting DNA size make the method less suitable for generating stable hESC clones.

Several strategies have been explored to circumvent the silencing effect of the integration site. The virus polyma mutant enhancer sequence PyF101 has been found to be resistant to silencing when it is located 5' to the CAG promoter and the transgene (GFP) retains expression in hESCs for over 120 passages (Liew C G et al. Stem Cells 2007; 25:1521-1528). Nevertheless, it is not shown if the GFP expression is sustained following cellular differentiation and if the PyF101 sequence is also effective for other promoters. Transgenes are introduced to some unique sites, such as the AAVS1 locus by adeno-associated virus type 2 (MV2) (Smith J R et al. Stem Cells 2008; 26:496-504) and the pseudo-attP sites by phiC31 integrase (Thyagarajan B et al. Stem Cells 2008; 26:119-126). However, the silence-resistant effect of these sites has not been studied in detail. The targeting efficiency of AAV2 is low (4.16%) and hESCs possess 23 different pseudo-attP sites, making it extremely difficult to screen the right and stable cell clones.

Several silence-resistant sites have been identified in the mouse genome, including ROSA26 (Zambrowicz B P et al. Proc Natl Acad Sci USA. 1997; 94:3789-3794), HPRT1 (Bronson S K et al. Proc Natl Acad Sci USA. 1996; 93:9067-9072) and ColA1 (McCreath K J et al. Nature 2000; 405: 1066-1069). Incorporation of a single copy of transgene expression cassette into these sites by a precise recombination mediated cassette exchange (RMCE) method has been demonstrated to be the best way in establishing transgenic cell lines and mice (Soukharev S et al. Nucleic Acids Res. 1999; 27:e21; Masui S et al. Nucleic Acids Res. 2005; 33:e43; Beard C et al. Genesis 2006; 44:23-28; Yu J et al. Genesis 2006; 44:252-261). Irion and colleagues inserted GFP under the ROSA26 promoter in hESCs through homologous recombination although they did not show if the ROSA26 promoter sustains GFP expression in terminally differentiated cells (Irion S et al. Nat. Biotechnol. 2007; 25:1477-1482). In rodents, ROSA26 promoter is insufficient to drive transgene (GFP) expression for direct visualization in brain tissue (Giel-Moloney M et al. Genesis 2007; 45:83-89). Neurons derived from transgenic mice and rats or mouse ESCs with transgene (GFP or alkaline phosphatase) inserted into the Rosa26 locus often do not exhibit transgene expression (Zhang, unpublished studies). Therefore, identification of an appropriate site for stable transgene expression not only in hESCs but also in their differentiated progenies remains to be solved.

SUMMARY OF THE INVENTION

To develop the present invention, we sought to screen and discover integration sites that are resistant to transgene silencing during hESC expansion and differentiation, especially in neural differentiation. In the screening vector, we built in a double loxP recombination exchange cassette, described by the Sauer group (Soukharev S et al. Nucleic Acids Res. 1999; 27:e21), so that the selected clone can serve as a master cell line. Replacement of the built-in loxP cassette with any targeting transgene cassette, possessing the same loxP sites through RMCE, allowed the generation of versatile transgenic hESC lines. A newly developed cell permeable Cre protein transduction method (Nolden L et al. Nat Methods 2006; 3:461-467) improved the efficiency of Cre-mediated recombination in hESCs. This technology and the master cell lines will make the establishment of transgenic hESC lines a laboratory routine. We envision that we may wish to create transgenic stem cell lines via insertion via Cre/Lox and non-Cre/Lox methods at the integration sites we have discovered.

In one embodiment, the present invention is a method of creating a human pluripotent transgenic stem cell line, comprising the steps of selecting a pluripotent stem cell line and inserting heterologous DNA at an insertion site selected from the group consisting of insertion site one and insertion site two to form a transgenic cell line (defined below). Site-directed homologous recombination can be used to introduce heterologous DNA at insertion site one or two by designing vectors that carry a reporter gene or gene of interest flanked by DNA sequences homologous to integration site one or two. The heterologous DNA can be vectors such as that described in Zwaka 20060128018 or Irion et al. (Nat. Biotechnol. 2007; 25:1477-1482). Preferably the heterologous DNA is a transgene. More preferably, the transgene is driven by a constitutive promoter, an inducible promoter or a cell type specific promoter.

In another preferred embodiment, the heterologous DNA is an exchange cassette and the transgenic cell line formed is a "master cell line", capable of swapping the marker gene material with other transgenic sequences of interest. More preferably the exchange cassette is a loxP exchange cassette. Even more preferably, the loxP exchange cassette comprises a double loxP sequence, a marker gene driven by a promoter and a selection gene. The promoter can be a constitutive promoter, an inducible promoter or a cell type specific promoter.

In another embodiment, the present invention is a method of creating a cell line comprising a transgene of interest, comprising the steps of exposing the master cell line (obtained using the exchange cassette as described for the above method) to a targeting vector comprising a second exchange cassette, wherein the second exchange cassette comprises a transgene of interest driven by a promoter, and selecting cells wherein the transgene of interest has integrated into the cell. Preferably, the exchange cassette is a loxP exchange cassette and the exposure of master cell line to a vector is in the presence of Cre recombinase. More preferably, the loxP exchange cassette is a double loxP cassette. The promoter driving the expression of the transgene can be a constitutive promoter, an inducible promoter or a cell type specific promoter.

In another embodiment, the present invention is a population of pluripotent stem cells comprising heterologous DNA integrated at an insertion site selected from the group consisting of insertion site one and insertion site two.

In another embodiment, the present invention is a population of pluripotent stem cells comprising an exchange cassette integrated at an insertion site selected from the group consisting of insertion site one and insertion site two. Preferably the exchange cassette is a loxP exchange cassette. More preferably, the loxP exchange cassette is a double loxP exchange cassette.

DESCRIPTION OF THE DRAWINGS

The patent or application file contains at least one drawing executed in color. Copies of this patent or patent application publication with color drawing(s) will be provided by the Office upon request and payment of the necessary fee.

FIG. 2. Sustained GFP expression following differentiation of the master hESCs in vitro and in vivo. The hrGFP expression was detected in all the ESC aggregates at day 6 (A), neuroepithelial cells in the rosettes at day 14 (B), TuJ1$^+$ neurons at 6 wks (C, D), and GFAP$^+$ astrocytes at 10 wks (E, F) during neural differentiation. The hrGFP expression was also observed in Brachyury T+ precursors at day 3 (I) and cTnT+ cardiac muscle cells at day 17 (J) during mesodermal differentiation, and in Sox17+ precursors at day 6 (M) and Pdx1+ pancreatic cells at day 17 (N) during endodermal differentiation. Teratoma analysis showed that GFP expression was sustained in neuroectodermal rosette cells (G, H), mesoderm derived muscle and cartilage (K, L), and endoderm derived epithelial tube (O, P). Bar=50 μm.

DESCRIPTION OF THE INVENTION

Introduction

Figure 1E:
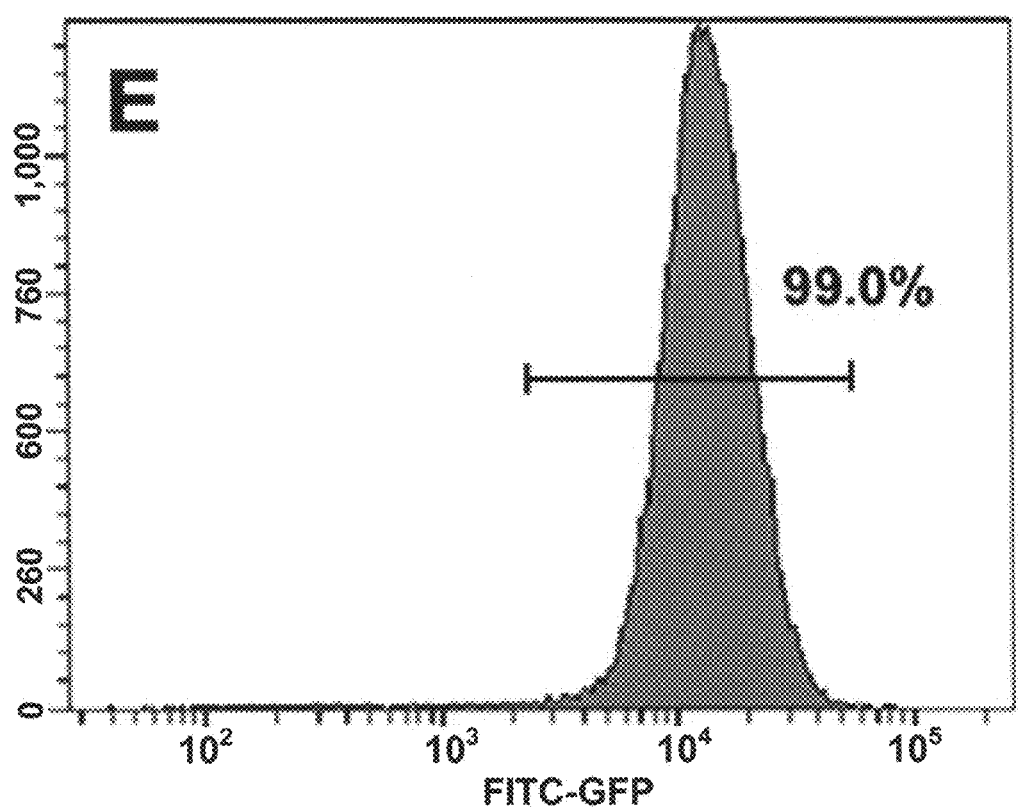
FIG. 1. Silencing-resistant master hESC lines with a built-in double loxP cassette. (A) Scheme of Cre-double loxP exchange system. The master ESC line was examined by phase contrast (B) and fluorescent illumination for hrGFP expression at passage 40 (C). Bar=50 μm. (D, E) Flow cytometric quantification of the hrGFP expression population. 99.0% SSEA4$^+$ ESCs showed hrGFP expression.

Building transgenic hESC lines with the most sophisticated technology has met with limited success. To date, there are few reports on the establishment of a stable hESC clone that sustains transgene expression during stem cell expansion and differentiation, with the exception of the GFP (green fluorescent protein) gene that is easy to monitor (Costa et al. Nat Methods 2005; 2:259-260; Liu et al. Stem Cells Dev. 2004; 13:636-645). Irion, et al. (Nat. Biotechnol. 2007; 25:1477-1482) disclosed the targeting of the double loxP cassette under the ROSA26 promoter locus to create an hESC cell line capable of genetic alteration. Their methods of modification of hESCs have limited success because the activity of human ROSA26 promoter in sustaining transgene expression has not been demonstrated especially in terminally differentiated cells. Even in rodents, ROSA26 promoter is insufficient to drive transgene (GFP) expression for direct visualization in the brain tissue (Giel-Moloney M et al. Genesis 2007; 45:83-

89). Neurons derived from transgenic mice and rats or mouse ESCs with transgene (GFP or alkaline phosphatase) inserted into the Rosa26 locus often do not exhibit transgene expression (Zhang, unpublished studies).

The difficulty of prior art methods stems from multiple levels, including low transfection and cloning efficiency (Eiges R et al. Curr Biol. 2001; 11:514-518, Zwaka T P et al. Nat. Biotechnol. 2003; 21:319-321) and high incidence of transgene silencing following integration into the host genome (Liew C G et al Stem Cells 2007; 25:1521-1528, Xia X et al. Stem Cells Dev. 2007; 16:167-176). At present, lentivirus mediated approach can achieve as high as 40-70% transfection efficiency in hESCs (Zhou B Y et al. Stem Cells 2007; 25:779-789; Xiong C et al. Stem Cells Dev. 2005; 14:367-377). However, its preference of integrating into the gene coding region, which poses a risk of insertional mutagenesis (Schroder A R W et al. Cell 2002; 110:521-529; Mitchell R S et al. PLoS Biol. 2004; 2:E234), and the DNA insertion size limitation make the method less suitable for generating stable hESC clones. The current status in genetic modification of hESCs presents a major roadblock to hESC research.

The Present Invention

We have found that one way to circumvent the roadblocks described above is to integrate the transgene by a site-directed recombination method into the specific "hot-spots" in the genome where stable and high gene expression may occur, such as the Rosa26 locus in the mouse genome (Zambrowicz B P et al. Proc Natl Acad U.S.A. 1997; 94:3789-3794). Such silencing-resistant integration sites in the hESC genome have not been clearly identified. Site-directed homologous recombination remains a technically challenging approach for building transgenic hESCs (Zwaka T P et al. Nat. Biotechnol. 2003; 21:319-321; Urbach A et al. Stem Cells 2004; 22:635-641). Even with the established technique in a limited number of laboratories, it has taken workers up to 1-2 years to build one line and the stability of the established hESC line has not been guaranteed.

A preferable method of inserting a transgene is via the Cre-Lox method. By "transgene" we mean any piece of heterologous DNA containing a gene sequence. In general, the Cre-Lox recombination system is a type of site-specific recombination that involves first inserting a loxP site that contains specific binding sites for Cre recombinase into a genome and then splicing in a new sequence. The new sequence will have been placed in a vector between loxP sites and will then be spliced in the presence of Cre recombinase.

More specifically, the Cre-Lox system is used as a genetic tool to control site specific recombination events in genomic DNA and has allowed researchers to manipulate a variety of genetically modifications to control transgene expression, delete undesired DNA sequences, and modify chromosome architecture. The Cre recombinase of bacteriophage P1 (the product of the cre gene) recognizes a specific 34 bp DNA sequence called loxP. Cre binds to these DNA sites and will bring them together in a synaptic complex. Conservative site-specific DNA recombination then ensues. We applied a "double loxP" strategy in the present invention (Soukharev S et al. Nucleic Acids Res. 1999; 27:e21), which provides an efficiency of targeting DNA vector exchange that is 20-100 fold more efficient than single loxP sites. The double loxP strategy is based on the observation that two loxP sites that differ in the center spacer region do not recombine whereas two loxP sites with the same spacer region recombine efficiently.

In the present invention, we screened for endogenous integration sites that are resistant to transgene silencing during hESC expansion and differentiation, especially neural differentiation. Our Examples below report two such successful sites in the human genome:

Insertion Site One: On chromosome 4q12, 34 kb from IGFBP7 gene and 30 kb from LOC255130 gene. The genomic nucleotide sequence immediately upstream of the inserted transgene is:

(SEQ ID NO:1)
TGCAATCTCCGCCTCCGGACTCAGGTGATTCTCCCACCTC.

Insertion Site Two: On chromosome 7q11.23, 22.5 kb from CLDN3 gene and 40 kb from CLDN4 gene. The genomic nucleotide sequence immediately upstream of the inserted transgene is:

(SEQ ID NO:2)
ACATAGGCATGATTGATTGCATCACTGGCCAATGGCAATC.

We will refer herein to these two integration sites as "Insertion Site One" and "Insertion Site Two".

In the master vector in the Examples, we built in a double loxP recombination exchange cassette, described by the Sauer group (Soukharev S et al. Nucleic Acids Res. 1999; 27:e21), so that the selected clone can serve as a master cell line. By "master cell line" we mean a cell line that, through exchange of transgenes, will allow the generation of versatile transgenic hESC lines. Preferably the exchange, through Cre-mediated recombination, is of a built-in loxP cassette with a targeting transgene cassette possessing the same loxP sites. This master cell line will be useful for creation of a variety of transgenic cell lines. For example, one may wish to create a simple reporter line or a line designed for conditional transgene expression. The present invention will make the establishment of transgenic hESC lines a laboratory routine once the master hESC line is in place.

The double loxP sites are useful for the master cell lines, as they showed 20-100 fold higher efficiency of targeted DNA exchange than a single loxP site. A newly developed cell permeable Cre protein transduction method (Nolden L et al. Nat Methods 2006; 3:461-467) was applied in our Example to improve the efficiency of Cre-mediated recombination in hESCs. The newly developed "cell permeable Cre protein transduction method" is a TAT protein transduction method, which is highly efficient in human ES cells compared to other methods that transfer a DNA vector expressing Cre (see Nolden, L et al. Nat Methods 2006; 3:461-467).

There are other double loxP sites suitable for the present invention, which typically have one or two different mutations in the center spacer region. loxP2272 and loxPN (Lee G et al. Gene 1998; 216:55-65; Livet J et al. Nature 2007; 450:56-62) are examples. Besides the Cre/loxP recombination exchange system we describe, there are other site specific recombination mediated exchange systems, such as FLP/Frt, integrase/att (Sadowski P., Nucleic Acids Res Mol. Biol. 1995; 51:53-91, Landy A., Annu Rev Biochem. 1989; 58:913-949), that are suitable for the present invention.

Thus, in one embodiment, the present invention provides a recombination exchange system for stable gene modification in human embryonic stem cells. In another embodiment, the present invention is a population of human ES cells with a transgene or a recombination exchange cassette at insertion site one or two.

Methods of the Present Invention
(i) Creating an hESC Master Cell Line

The method of the present invention begins with the selection of a human embryonic stem cell. By "human embryonic stem cell", Applicants mean to include stem cells that have been isolated from human embryos, such as the hESC line H9 that we used below in the Examples. Other suitable human embryonic stem cell lines would be among those listed in the NIH Human Embryonic Stem Cell Registry, such as ES01-06 from ESI (ES Cell International, 11 Biopolis Way, # 05-06 Helios, Singapore 138667), UC01, UC06 from UCSF (University of California at San Francisco).

Applicants also intend to include "reprogrammed" human embryonic stem cells as within the scope of "Human Embryonic Stem Cell", such as described in J. Yu, et al. (Science 2007; 318:1299-1302), Takahashi et al. (Cell 2006; 126:663-676) and Nakagawa M. et al. (Nat. Biotechnol. 2008; 26:101-106). The recombination exchange system would work equally well with differentiated cells that have been reprogrammed and exhibit the characteristics of traditionally prepared human embryonic stem cells. These characteristics are defined in U.S. Pat. Nos. 5,843,780, 6,200,806 and 7,029,913 as the following cell surface markers: SSEA-1 (−); SSEA-4 (+); TRA-1-60 (+); TRA-1-81 (+); and alkaline phosphatase (+) and SSEA-1 (−); SSEA-3 (+); SSEA-4 (+); TRA-1-60 (+); TRA-1-81 (+); and alkaline phosphatase (+). Additionally, ES cells are capable of continuous indefinite replication in vitro in an undifferentiated state. The cells have normal karyotypes, which include the presence of the chromosomes characteristic of the primate species. None of the chromosomes are noticeably altered. The cells also retain the ability to form trophoblast and produce chorionic gonadotropin. These cells also differentiate into all tissues derived from all three embryonic germ layers (endoderm, mesoderm and ectoderm).

The method of the present invention typically comprises the following steps:

First, one would prepare the master vector. The master vector preferably comprises a loxP integration cassette comprising double loxP sites (see Soukharev S et al. Nucleic Acids Res. 1999; 27:e21), a marker gene driven by a promoter, and an antibiotic selection cassette, preferably the GFP expression cassette driven by CAG promoter and neomycin selection cassette. By "loxP integration cassette" we mean a double loxP site comprising a typical double loxP cassette comprises two different loxP sites that differ in center spacer region and do not recombine with each other. By "marker gene" we mean any gene or sequence that can be detected after integration. For example, the GFP marker gene can be detected by evaluation of fluorescence. "Promoter" can be any constitutive promoter which is active universally in many cell types, such as EF1α (elongation factor 1α) promoter and PGK (phosphoglycerate kinase 1) promoter. "Selective antibiotics" can be any antibiotics which can function in selecting mammalian cells. (If one wished to use another recombination exchange system, one would, of course, use the components for that system.)

One then transfects hESCs with the master vector, preferably by electroporation.

The GFP positive hESC clones are selected after drug selection, and one then selects the hESC clones with single integration copy. We use the qPCR method to determine the integration copy number, which showed a single copy in the master cell lines. We used the Site-finding PCR method to determine whether the GFP master vector was inserted into integration site one or two in the two master cell lines (see Tan G H et al. Nucleic Acids Res. 2005; 33:e122).

If desired, one selects the hESC clones with stable GFP expression during different types of cell differentiation. Preferably, one confirms that the integration site does not disrupt an endogenous gene. If one wants to create the master cell line of the present invention, one may typically apply the homologous recombination method as shown in Irion et al. (Nat. Biotechnol. 2007; 25:1477-1482). According to the DNA sequences of the integration site one or two, one would design the vector having the double loxP cassette (or other type of integration cassette) flanked with homogenous DNA sequences at both sides of integration site one or two, and then transfect the vector into hESCs by eletroporation, select the cell clones and examine the cell clones having double loxP cassette inserted in integration site one or two. Since transgenes introduced into these two sites are not silenced in human cells, including functionally mature neurons, these two sites can be targeted for introducing DNA for gene therapy. This will avoid the typical silencing effect of transgenes in human cells.

(ii) Use of an hESC Master Cell Line to Provide Transgenic hESC Lines

Once one has obtained the hESC master cell line, one may wish to exchange the marker gene used to create the master cell line with a gene or sequence of interest to provide a specific transgenic hESC line. In one embodiment, one would exchange the marker gene with a selected gene or sequence in the following manner.

1. Prepare a targeting vector with the desired gene as described above, which is very similar to the master vector but the desired gene has replaced the marker gene via antibiotic selection. The master vector and targeting vector each have a different antibiotic selection markers. We chose neomycin and hygromycin which are regularly used in mammalian cells. There are other selective antibiotics available from commercial sources, such as Invitrogen, for example, blasticidin, G418, phleomycin, puromycin and zeocin. Accordingly, genes conferring resistance to any of these antibiotics can be used as selection genes.

2. Transfect the master hESC line with the targeting vector using Fugene reagent, and treat with TAT-Cre. "Fugene reagent" is a chemical transfection reagent sold by Roche Applied Science. TAT-Cre is a fusion protein prepared by bacteria expression system (see Wadia J S et al. Nat. Med. 2004; 10:310-315). We used the Fugene reagent to transfect the target vector into the master cell line, then apply TAT-Cre protein to induce recombination. One may co-transfect the target vector and Cre-expressing vector into the master cell line by electroporation method as shown in Irion, et al. (Nat. Biotechnol. 2007; 25:1477-1482). However, our method is much more efficient.

3. Select the marker-gene-negative hESC clones after antibiotic selection.

4. Confirm the exchanged cell clone by PCR and further analysis.

Cell Populations of the Present Invention

In one embodiment, the present invention is a population of hESC comprising an integration cassette, such as a double loxP recombination exchange or "master" cassette, wherein the exchange cassette is integrated at integration sites one or two. In another embodiment, the present invention is a stem cell or cell line wherein a transgene has integrated at insertion site one or two.

EXAMPLES

Example 1

Creation of Transgenic hESC Line

We described a transgene integration strategy employing the recombination mediated cassette exchange (RMCE) system for establishment of human embryonic stem cells (hESC) lines carrying versatile transgenic modification. Two master hESC lines with a built-in double loxP recombination exchange cassette were screened out to integrate into new silencing-resistant sites and to sustain the transgene (GFP) expression during differentiation into cells representing the three germ layers. Using a cell permeable Cre protein transduction method, the double loxP cassette in the master cell lines was successfully and specifically exchanged with multiple targeting transgene cassettes, including constitutive functional gene expression, cell lineage specific reporter gene expression and inducible transgene expression. This strategy and the master cell lines will allow for rapid production of transgenic hESC lines, thus facilitating analysis of gene function involved in early human development and potentially in pathological processes.

Results

1. Silencing-Resistant hESC Lines are Selected with a Built-in Double loxP Exchange Cassette.

Figure 7:
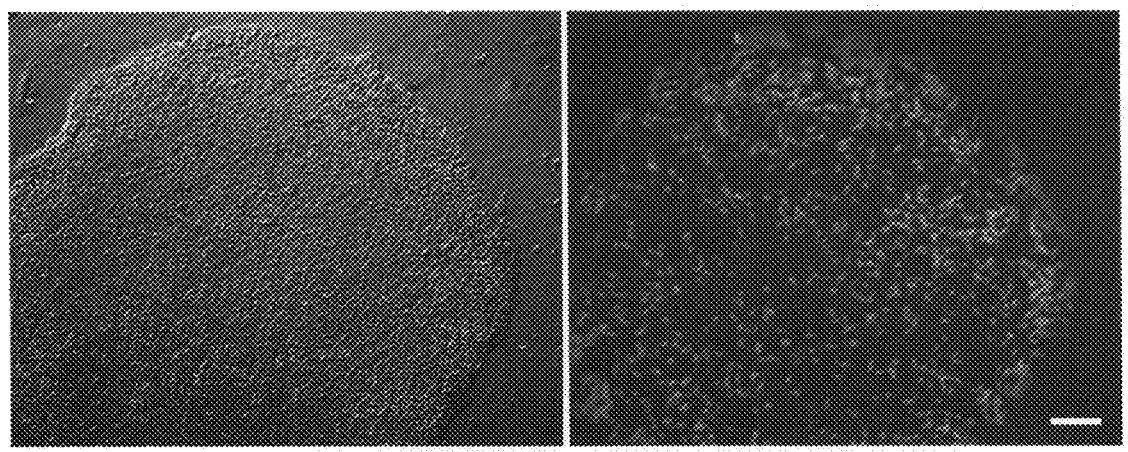
FIG. 7. A representative hESC clone showed variegated GFP expression. Bar=50 μm.

We have shown previously that transgenes are severely suppressed immediately following infection by lentivirus in hESCs (Xia X et al. Stem Cells Dev. 2007; 16:167-176). In this study, transfecting hESCs with the plasmid containing hrGFP (humanized renilla green fluorescent protein) driven by the CAG (cytomegalovirus immediate early enhancer/chicken beta-actin promoter) promoter and neomycin resistance gene driven by PGK promoter resulted in dozens of stable neo-resistant cell clones. However, only 17 of the total 98 (17.3%) clones expressed GFP (three independent experiments), and some clones showed variegated GFP expression (FIG. 7). Parallel experiments using the same construct to transfect mouse ESCs indicated that 211 of 254 (83.1%) cell clones expressed GFP (Table 1). This result suggests that the expression of transgenes randomly integrated into the human ESC genome will be largely silenced.

To circumvent the silencing effect of integration sites on transgene expression in hESCs, we screened silencing-resistant sites using a vector with a built-in double loxP sites. The strategy consists of two steps (FIG. 1A). In the first step, the expression cassettes of hrGFP gene driven by CAG promoter and the neomycin resistance gene driven by PGK promoter are flanked by loxP and lox2272 sites to make the master vector. The wild type loxP and mutant lox2272 sites are designed not to recombine with each other, but they can undergo recombination with the same site in the targeting vector. The master vector is transfected into hESCs, and the hESC clones, which show ubiquitous and stable GFP expression during expansion and differentiation, will be selected as a master cell line. In the second step, a new transgene driven by CAG (or any other) promoter and the hygromycin resistance gene driven by the PGK promoter are flanked by loxP and lox2272 sites to make the targeting vector. When co-transfecting with Cre recombinase into the master hESCs, the targeting vector can replace the master vector at the same integration site, which guarantees the silence-resistant expression of the new transgene as that of GFP.

Linearized master vector was transfected into the hESCs (H9 cell line) by electroporation. After selecting with neomycin for two weeks, 228 resistant cell clones were produced from six transfection experiments. 17 clones were selected with uniform GFP expression in hESCs through regular passaging (FIGS. 1B, C). FACS analyses with the hESC marker SSEA-4 indicated that 97%-99% of the SSEA-4 positive hESCs showed GFP expression (FIGS. 1D, E), confirming the uniform expression pattern of GFP and the stem cell state of the transgenic cells.

For effective Cre-RMCE, it is ideal to have only one integration copy of the master vector in the genome of the master hESC line. We applied the qPCR method to determine the copy numbers of the hrGFP gene relative to the control GAPDH gene. Among the 17 clones, 8 clones had one integration copy, another 8 clones had two integration copies, and one clone had about one and half integrating copies (Table 2).

2. The Master hESC Line is Selected to Sustain GFP Expression During Differentiation.

A master hESC line should possess stable transgene (GFP) expression not only during stem cell expansion but also along differentiation into cells of the three germ layers. The above 8 clones with one integration copy were first differentiated to neuroectodermal cells in our chemically defined system (Zhang S C et al. Nat. Biotechnol. 2001; 19:1129-1133). Two clones showed uniform GFP expression in the hESC aggregates at day 6 and in the neuroepithelial cells in the form of rosettes at day 12 following hESC differentiation (FIGS. 2A, B). In additional 4 and 8 weeks of differentiation, the majority of TuJ1 positive neurons and GFAP positive astrocytes retained GFP expression (FIGS. 2C-F). When the two hESC clones were differentiated toward the mesoderm cell lineages, GFP expression was sustained in Brachyury T+progenitor cells at day 3 and cTnT$^+$ (cardiac troponin T) beating cardiac muscle cells at day 17 (FIG. 2L, J). Similarly, GFP expression was sustained in Sox17$^+$ endoderm progenitor cells and Pdx1+ endoderm-derived pancreatic cells following 6 days and 17 days of hESC differentiation, respectively (FIGS. 2M, N). Analysis of the teratomas formed from the two cell lines 2 months after injection showed ubiquitous and stable GFP expression in the neuroectoderm (FIGS. 2G, H), mesoderm derived muscle and cartilage (FIGS. 2K, L), and endoderm derived epithelial tube (FIGS. 2O, P). These results confirm that GFP expression in the two hESC lines is not silenced following differentiation to cell types representing the three germ layers both in vitro and in vivo.

Figure 8:
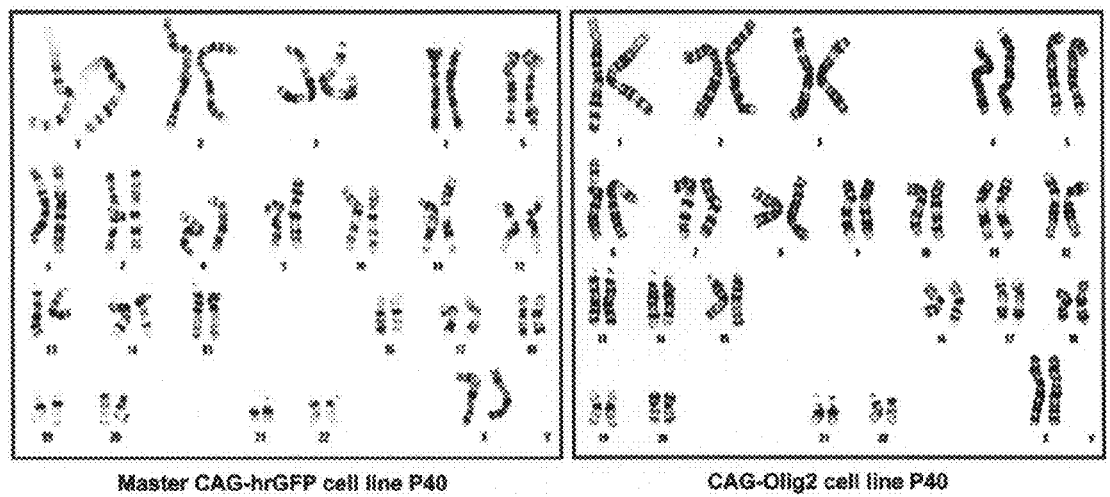
FIG. 8. The master CAG-hrGFP cell line and exchanged CAG-Olig2 cell line showed normal karyotype at passage 40

Besides resistance to gene silencing, the integration site of the master vector should not interfere with the expression of endogenous genes. Site-finding-PCR analysis (Tan G et al. Nucleic Acids Res. 2005; 33:e122) indicated that in one clone the master vector was integrated in chromosome 4, between the gene loci IGFBP7 and LOC255130, and in the other clone the master vector was integrated in chromosome 7, between the gene loci CLDN3 and CLDN4. Based on DNA sequence blast analyses, these two loci are not in the gene coding region or known gene regulatory elements. These two hESC lines sustained GFP expression and retained normal karyotype after expanding for more than 40 passages (FIG. 8). Therefore, they were finally selected as the master hESC lines for later RMCE experiments.

3. Specific Cassette Exchange is Mediated by Cell Permeable Cre Protein.

Figure 3A:
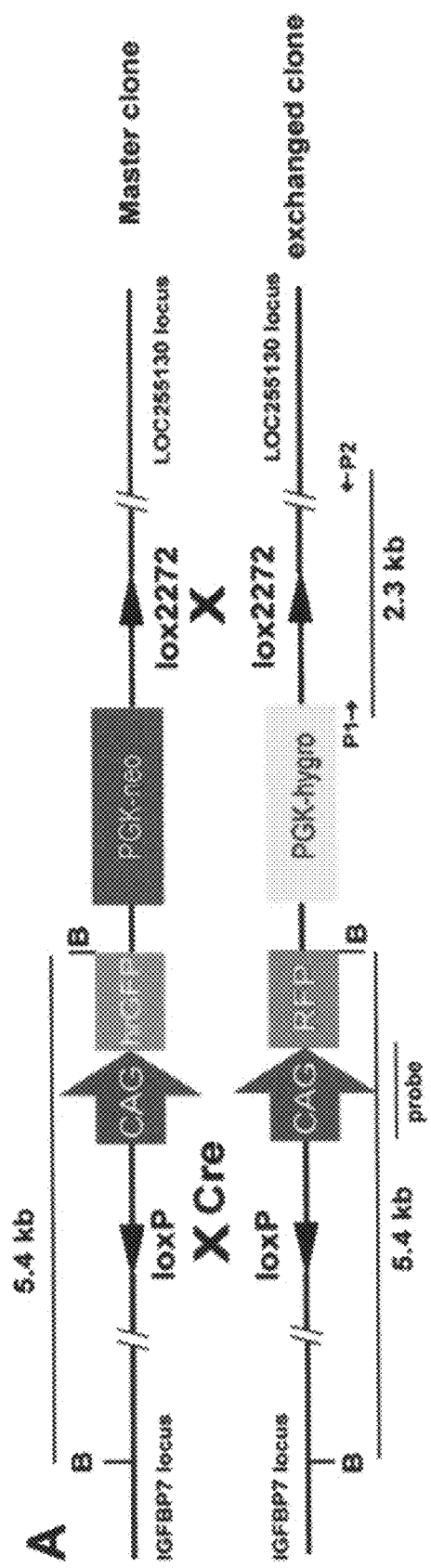
FIG. 3. Replacement of the master GFP cassette with the targeting RFP cassette through RMCE. (A) Scheme of cassette exchange before and after RMCE. The sizes of DNA fragments from PCR and Southern blotting analysis were indicated. B, BamHI site. The correctly exchanged cell clones showed loss of GFP (B) and gain of RFP expression (C). Some un-exchange cell clones showed co-expression of GFP and RFP (D, E). The correctly exchanged clones were confirmed by PCR (F) and Southern blotting analysis (G). RMCE exchanged clones displayed the same restriction pattern as that in the master cells, a specific 2.3 kb PCR-amplified band and a 5.4 kb BamHI -digested fragment whereas the un-exchanged clones showed no PCR-amplified band but an extra BamHI-digested fragment.

To test whether the double loxP cassette in the master hESCs can be exchanged specifically, we constructed a double loxP targeting vector with RFP (red fluorescent protein) expression driven by CAG promoter and hygromycin resistant gene driven by PGK promoter (FIG. 3A). The targeting vector and the Cre expression vector were co-transfected into the master hESC lines by the lipofection or electroporation method, both of which were successfully used in the RMCE experiments of mouse ESCs (Soukharev S et al. Nucleic Acids Res. 1999; 27:e21; Call L M et al. Hum Mol. Genet. 2000; 9:1745-1751). After selecting with hygromycin B for two weeks, most of the produced clones were still GFP positive. Few of the clones (2 out of 92 clones from three transfections) showed loss of GFP, indicating that site-specific recombination to replace the master GFP cassette with the RFP expression cassette is not efficient. This is likely due to the overall low transfection efficiency for both vectors in hESCs, leading to the rare coexistence of the Cre recombinase and the targeting vector.

Figure 9:
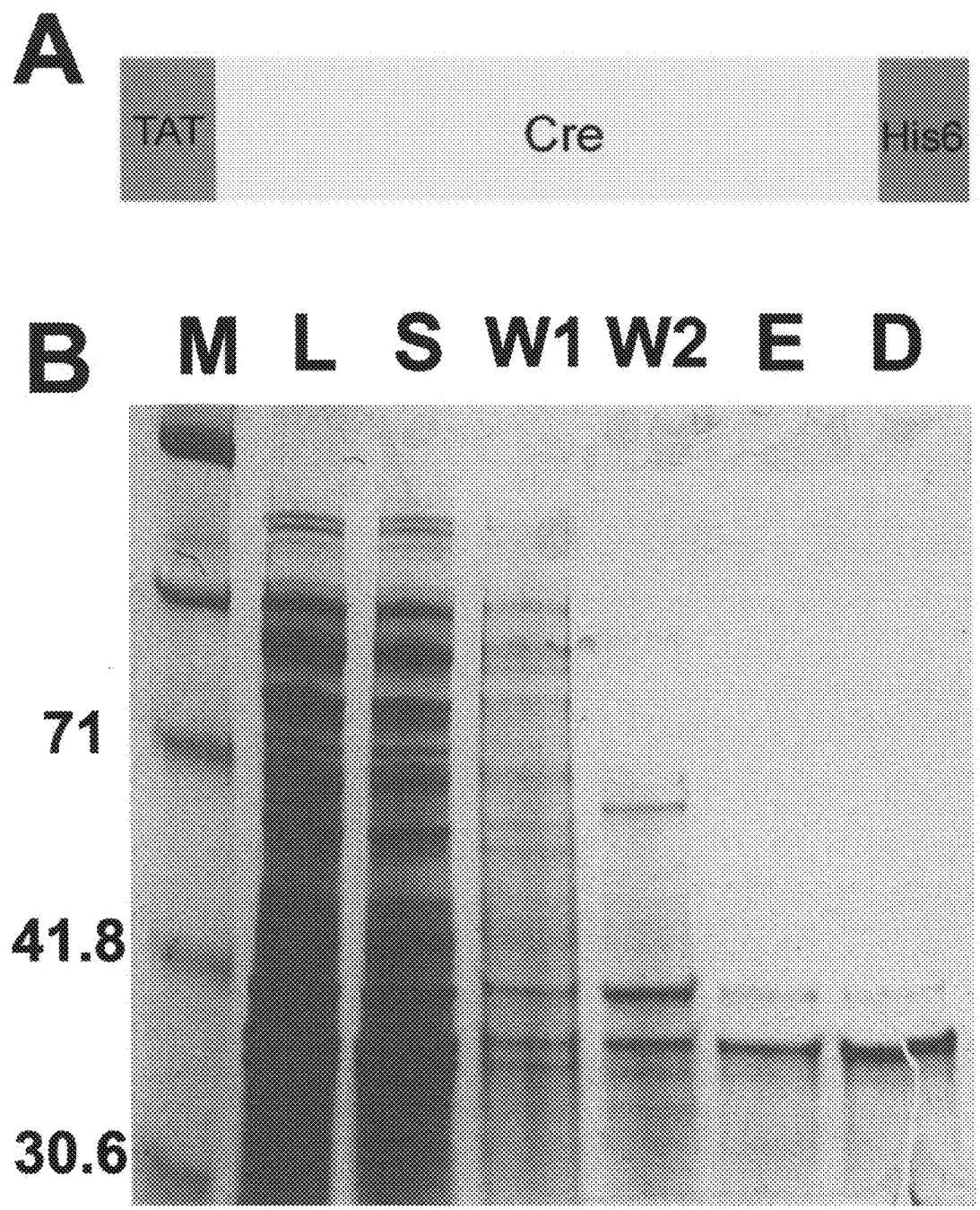
FIG. 9. (A) Schematic structure of the TAT-Cre fusion protein. (B) Purification of the cell permeable TAT-Cre fusion protein, as analyzed by Coomassie blue staining of an SDS-PAGE gel. M, protein standard marker; L, lysate; S, supernatant; W1, W2, wash fraction 1 and 2; E, elution fraction; D, dialysis fraction.

RMCE in hESCs may be significantly enhanced by applying the cell permeable Cre protein directly to the cells (Nolden L et al. Nat Methods 2006; 3:461-467). TAT-Cre, a fusion protein combining the protein translocation peptide derived from HIV-TAT with Cre recombinase, was expressed and purified in a bacteria expression system (FIG. 9). The targeting vector for RFP expression was first transfected into the master hESCs by Fugene®HD reagent, and then the TAT-Cre protein was added into the culture medium 5 hours later. Under this condition, an average of 18 hygromycin resistant clones in one transfection experiment (three 30 mm-wells) were produced after 2 weeks of selection. Six clones showed loss of GFP and gain of RFP expression (FIGS. 3B, C), a sign of correct RMCE in the master hESCs. Two clones showed the loss of GFP but without the RFP, suggesting non-specific recombination. The remaining clones showed co-expression of GFP and RFP, suggesting that the cassette was un-exchanged and the RFP targeting vector randomly integrated in the master hESCs (FIGS. 3D, E). PCR analysis using primers located on the targeting vector and the integrating locus showed the specific band for the exchanged cell clones (FIG. 3F), which will be used to identify the correctly exchanged cell clones in the later RMCE experiments. Southern blotting analysis indicated that the exchanged cell clones and the master cell line exhibited the same band whereas the unexchanged cell clones displayed extra restriction fragments (FIG. 3G), confirming the specificity of the RMCE.

Figure 4A:
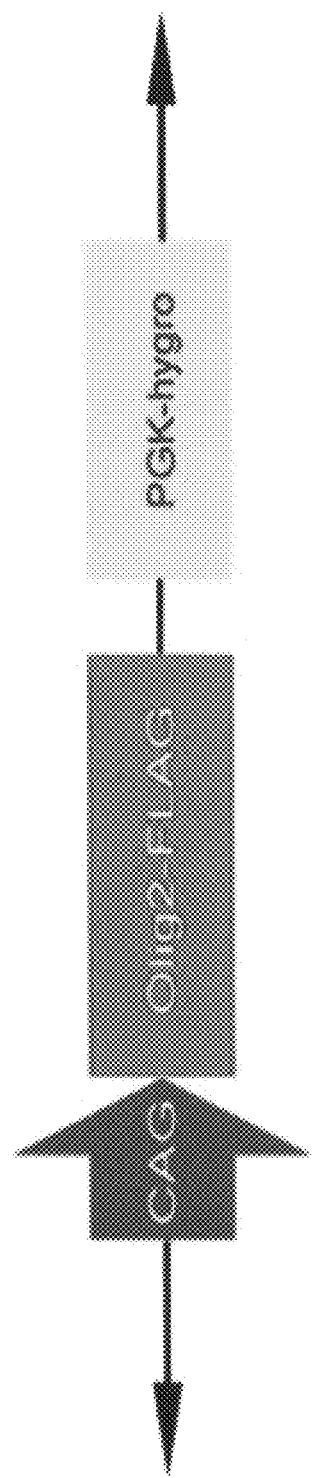
FIG. 4. hESC line with functional Olig2 gene expression. (A) Structure of the Olig2-FLAG targeting vector. (B) FLAG staining was present in all cells when the exchanged Olig2-FLAG expressing cells were differentiated to neuroepithelial cells (rosette) for 14 days. The Olig2 expression was detected in the nestin$^+$ neural precursor cells (C), but not in the parental H9 cells differentiated at the same period (D). Following differentiation to motor neurons at the 5$^{th}$ week, the parental H9 cells generated many HB9$^+$ motor neurons (E) whereas the Olig2-expressing cells produced few HB9$^+$ neurons (F). Bar=50 μm. (G) Quantification of HB9$^+$ motor neurons.

4. Versatile Transgenic hESC Lines are Established Via RMCE (1) Human ESC Lines with Constitutive Expression of a Functional Gene To test whether a transgene in the targeted hESCs will be functional, we chose to express Olig2, a transcription factor that is critical for the differentiation of spinal motor neurons from ESCs (Li XJ et al. Nat. Biotechnol. 2005; 23:215-221; Wichterle H et al. Cell 2002; 110:385-397). The Olig2 targeting vector (FIG. 4A) was transfected into the master cell line to replace the master vector. Two hESC clones were established following the procedure described above. Following 14 days of neural differentiation, all the differentiated neural precursor cells in the rosette structure were positively stained for FLAG (FIG. 4B). Immunostaining for Olig2 confirmed that all cells, including the nestin+ neural precursor cells, expressed Olig2. In contrast, neural precursors differentiated from the parental H9 hESCs did not express Olig2 under this condition (FIGS. 4C, D).

To determine if the transgenic Olig2 is functional, we differentiated the transgenic and parental H9 hESCs to spinal motor neurons using our established protocol (Li X J et al. Nat. Biotechnol. 2005; 23:215-221). Transcription of Olig2 is essential for specification of motor neuron progenitors, but sustained high-level expression of Olig2 represses the generation of post-mitotic motor neurons marked by HB9 expression. Similar to our previous finding, HB9-expressing post-mitotic motor neurons began to appear after 4 weeks of differentiation in the presence of retinoic acid and sonic hedgehog in the parental hESCs, and reached a peak at the 5$^{th}$ week in which about 40% of total cells were positive for HB9 (FIG. 4E). However, in the Olig2 transgenic cell lines, less than 5% of the differentiated cells showed expression of HB9 and these HB9 positive cells also showed the down-regulation or the loss of the expression of transgenic Olig2 (FIGS. 4F, G). This result is consistent with the finding in mouse experiments that sustained high-level expression of Olig2 blocks the generation of the HB9+ post-mitotic motor neurons (Lee S K et al. Genes Dev. 2005; 19:282-294). This result suggests that forced Olig2 expression in the hESCs, established through RMCE from the master cell line, bears functional consequence.

(2) Human ESC Lines with Inducible GFP Expression

We explored the possibility to build hESCs with inducible transgene (GFP) expression by exchanging the constitutive expression vector in the master line with an inducible GFP expression vector. The single-vector strategy described by Szulc et al. (Szulc J et al. Nat Methods 2006; 3:109-116) was applied, which takes advantage of the promiscuous repression activity of tTRKRAB, a fusion protein of the Kruppel-related box (KRAB) domain and the tetracycline repressor (tetR), which represses the activity of promoters located within the 2-3 kb region of the tet operator (TetO) sequence and can be regulated by tetracycline. The inducible targeting vector (FIG. 5A) was transfected into the master hESC lines to replace the master vector with the treatment of TAT-Cre protein. After selection with hygromycin B for two weeks, we picked out two cell clones with negative GFP expression. When treated with doxycycline (Dox, 1 ug/ml), GFP was observed uniformly in the hESC colonies 48 hours later (FIGS. 5B, C), indicating inducible GFP expression.

Figure 5:
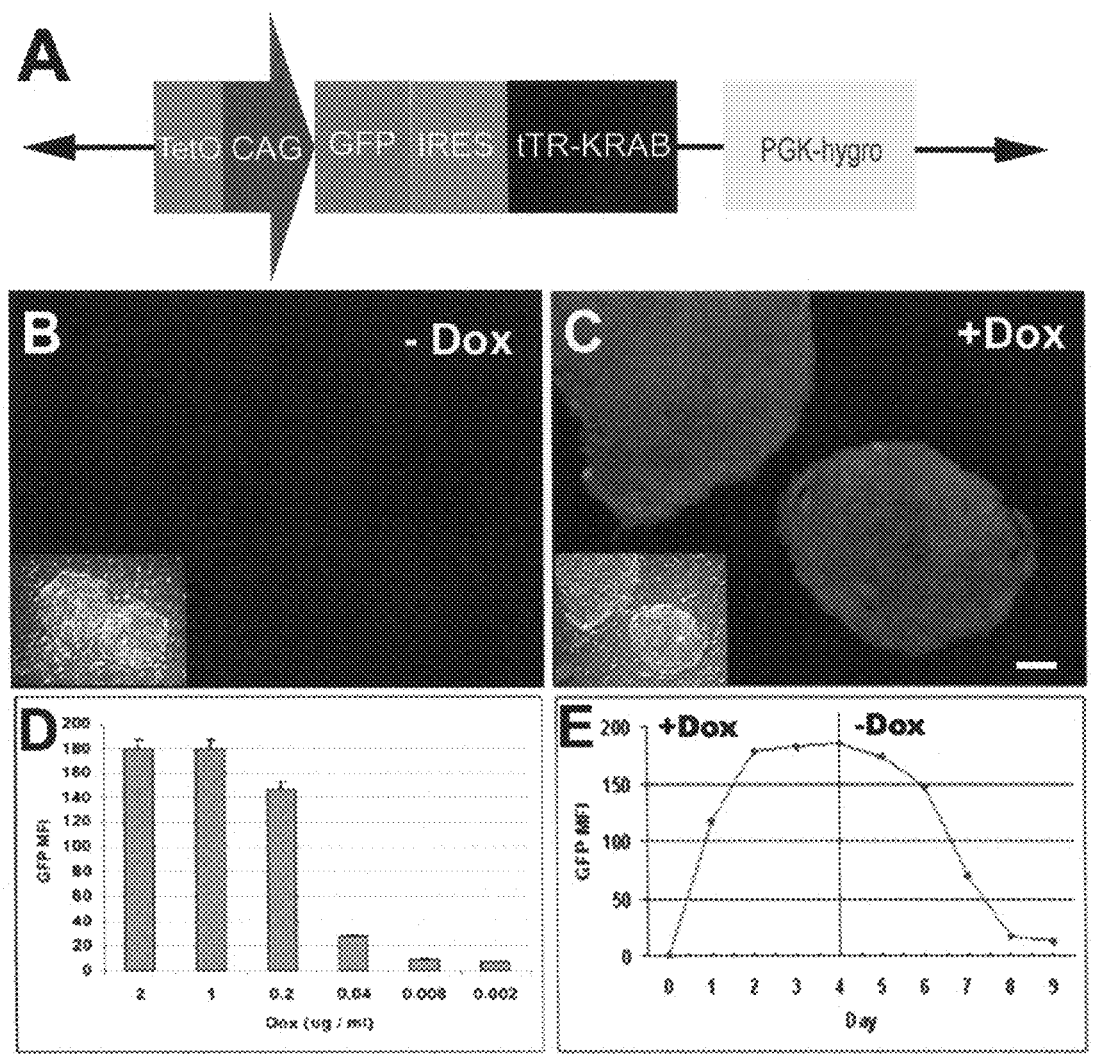
FIG. 5. hESC lines with inducible GFP expression. (A) Design of the inducible GFP targeting vector. Following the exchange of the loxP cassette, GFP was negative without Dox treatment (B), and was turned on when treated with 1 ug/ml Dox for 48 hrs (C). Bar=50 μm. (D) Dox dose-dependent analysis of the inducible ESC line. (E) The kinetics of GFP induction and degradation in the inducible ESC line.

To determine whether GFP expression level may be regulated in a dose-dependent manner, the inducible ESC lines were treated with different doxycycline concentrations (2 µl, 0.2, 0.04, 0.008, and 0.002 ug/ml). FACS analysis of the GFP intensity 3 days after Dox treatment indicated that the GFP expression was dose-dependent within the range of 0.002-1 ug/ml of Dox (FIG. 5D). To determine the kinetics of GFP expression in response to doxycycline, the hESC cultures were treated with the optimal doxycycline concentration (1 ug/ml) for 1, 2, 3, and 4 days. FACS analysis showed that the maximum level of GFP was reached in nearly all the hESCs by Day 2. At day 4, when the GFP expression was stable, doxycycline was then withdrawn from the cultures. Daily FACS measurements indicated that the GFP disappeared completely in the hESCs after 5 days of Dox withdrawal (FIG. 5E).

(3) Human ESC Lines with Neuron Specific GFP Expression.

Figure 6:
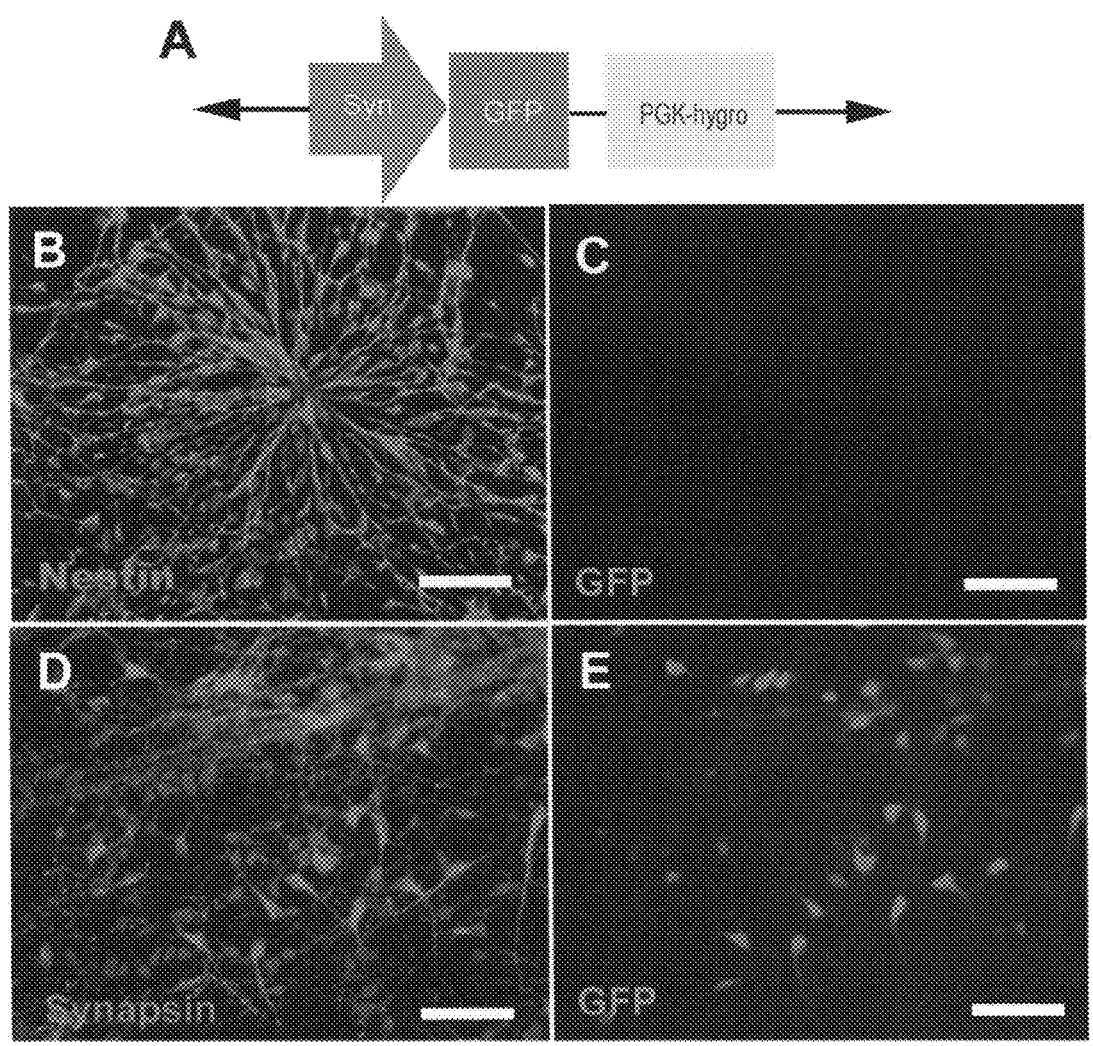
FIG. 6. hESC lines with neuron specific GFP expression (A) Schematic diagram of the targeting vector with GFP expression driven by the Synapsin promoter. The Syn-GFP ESC line did not show GFP expression in nestin$^+$ neuroepithelial cells at day 14 (B, C), but displayed the GFP in synapsin$^+$ maturing neurons after further differentiation at day 35 (D, E). Bar=25 μm. Blue represent Hoechst stained nuclei.

In practice, it is often necessary to restrict the transgene expression in a particular cell type. This may be achieved through the use of cell type-specific promoters, such as synapsin for neurons. In principle, the silence-resistant sites we identified may also function for other transgene expression such as cell type-specific promoters. To provide proof-of-principle, we constructed a targeting loxP vector by replacing the CAG promoter in the master vector with the synapsin promoter (FIG. 6A). In this way, the GFP will be turned on only when the hESCs differentiate to synapsin-expressing neurons. The hESCs can also serve simply as a neuronal reporter line.

Two different Syn-GFP cell lines were established from the master cell lines after Cre mediated exchange with the master vector described above. The newly established hESCs did not exhibit GFP. When induced for differentiation along the neural lineage, GFP was not observed in the ESC aggregate stage at day 6 or at the nestin-expressing neuroepithelial stage at day 14 (FIGS. 6B, C). GFP began to appear after the expanded neuroepithelial cells were differentiated to neurons in the serum-free medium at day 28. Along further differentiation, GFP expression was seen in synapsin+ neurons (FIGS. 6D, E). Thus, the GFP is specifically expressed in the maturing neurons.

Discussion:

At the present study we have identified at least two sites that allow stable transgene expression not only during the expansion of hESCs, but also in their differentiated progenies representing the three germ layers in vitro and in vivo. To enable the making of transgenic hESC lines in an ordinary laboratory, we have built master hESC lines that carry a unique double loxP exchange cassette. By replacing the loxP cassette with a targeting vector through Cre RMCE, we have built transgenic hESC lines expressing a functional gene, conditionally expressing a transgene, or incorporating a reporter gene in a cell lineage specific pattern. These master hESC lines with a built-in double loxP cassette, together with the permeable Cre protein-mediated recombination demonstrated here, shall significantly facilitate the generation of transgenic hESC lines in a substantially shorter period.

Stability of transgene expression is highly dependent on the site of integration (Bronson S K et al. Proc Natl Acad Sci USA. 1996; 93:9067-9072; Grosveld F et al. Cell 1987; 51:975-985). Several silence resistant sites have been identified in transgenic mouse studies, such as ROSA26 and HPRT1. Although these loci are conserved between human and mouse, the silencing resistant effect on exogenous promoters inserted into the ROSA26 and HPRT1 loci has never been examined in human. Costa et al. identified one "Envy" site on chromosome 7 to retain the robust GFP expression in hESCs and differentiated progeny using a similar construct as our master vector (Costa M et al. Nat Methods 2005; 2:259-260), suggesting the possibility of identifying the new silence-resistant site in hESCs. However, they didn't build the recombination mediated cassette exchange system in the "Envy" site to express other transgenes. The two sites we identified through our laborious screening appear to sustain functional transgene expression along differentiation. Genomic blast analyses suggest that these two sites will unlikely affect endogenous gene expression. Our studies indeed show no observable changes in the growth, maintenance, directed in vitro differentiation, and teratoma formation in vivo. While we have shown that these sites sustain expression of GFP and some functional genes in differentiated neural cells, more extensive analysis is needed to verify whether these sites can serve as universal sites for transgene expression in functional human cells of other lineages.

With a known site for stable transgene expression, one may build transgenic hESC lines through homologous recombination. However, site-directed integration of transgenes into these sites via homologous DNA recombination in hESCs remains a laborious and challenging task for an ordinary laboratory, only a few successful homologous recombinations in hESCs have been reported (Zwaka T P et al. Nat. Biotechnol. 2003; 21:319-321; Irion S et al. Nat. Biotechnol. 2007; 25:1477-1482; Urbach A et al. Stem Cells 2004; 22:635-641; Costa M et al. Nat. Protoc. 2007; 2:792-796). Our master hESC lines with the Cre RMCE system eliminate the need for screening a large number of cell clones. We hope that versatile transgenic hESC lines may be built upon these master hESC lines by most laboratories.

Our system for establishing transgenic hESC lines depends on high efficient Cre RMCE, however, the efficiency of Cre-mediated recombination by traditional co-transfection remains low in hESCs. This is at least partly due to the low transfection efficiency, leading to the rare co-existence of the Cre recombinase and the targeting vector. By using the newly developed cell permeable Cre protein transduction method (Nolden L et al. Nat Methods 2006; 3:461-467), we showed about 30% recombination efficiency. This is comparable to the RMCE efficiency in mouse ESCs (Adams L D et al. Brain Res Mol Brain Res. 2003; 110:220-233). Use of cell permeable Cre protein temporarily and at a low concentration is also beneficial to the hESC growth and karyotype stability, as Cre recombinase is known to have possible toxic effects that can compromise normal cell cycle and survival (Loonstra A et al. Proc Natl Acad Sci USA. 2001; 98:9209-9214; Fomi P E et al. J. Neurosci. 2006; 26:9593-9602).

Together, the master hESC lines with the double loxP exchange cassette and RMCE via the cell permeable Cre protein transduction method offer a flexible and simple platform for genetic manipulation of hESCs. First, a transgenic cell line can be easily obtained by Cre recombination mediated exchange with a target gene of interest. Second, a series of different genes may be introduced into the same integration site to evaluate gene function without the variation in the level and pattern of gene expression. The master hESC lines were deposited to the WiCell Institute/the U.S. National Stem Cell Bank for distribution. The availability of these versatile tools will change the way we study human stem cells.

Methods:

Maintenance and Differentiation of hESCs

Human ESC lines, H9 (NIH Code WA09, passages 17 to 45) was cultured and passaged every 6 days on a feeder layer of irradiated embryonic mouse fibroblasts as described (Thomson J A et al. Science 1998; 282:1145-1147). Differentiated colonies were physically removed before passaging and the undifferentiated state of ESCs was confirmed by typical morphology and uniform expression of October4 and SSEA4. The established master hESC lines were examined by karyotype analysis (WiCell Institute) to make sure that the genetically modified ESCs retain the normal genetic background. The procedure for differentiation to neural precursors and motor neurons from hESCs was essentially the same as described (Zhang S C et al. Nat. Biotechnol. 2001; 19:1129-1133; Li X J et al. Nat. Biotechnol. 2005; 23:215-221). The procedures for endoderm and mesoderm differentiation were from the published protocol (D'Amour K A et al., Nat. Biotechnol. 2005; 23:1534-1541).

Vector Construction

The double loxP containing vector pLox was constructed by replacing the lox511 site in pSS66 plasmid (Soukharev S et al. Nucleic Acids Res. 1999; 27:e21) with lox2272 site by PCR cloning. The antibiotics resistant cassette PGK-neo and PGK-hygromycin from pBS524 and pBS528 was inserted into the EcoRV site of pLox to make the pLox-neo and pLox-hyg vector. To construct the master vector, CAG-hrGFP cassette was inserted into the EcoRV site of pLox-neo vector. For RFP targeting vector, CAG-RFP cassette was inserted into the EcoRV site of pLox-hyg vector. For the Olig2 targeting vector, the Olig2-FLAG cDNA (gift from Prof. Nakafuku) was used to replace the hrGFP in CAG-hrGFP, and then the CAG-Olig2-FLAG was inserted into the EcoRV site of pLox-hyg vector. For Syn-GFP targeting vector, Syn-GFP cassette from pMH4-1-SYN-EGFP (gift from Prof. Kugler) was cloned into the EcoRV site of pLox-hyg vector. For the inducible GFP targeting vector, the tetO sequence from pLVTHM (Addgene plasmid 12247) (Nolden L et al., Nat. Methods 2006; 3:461-467) was inserted into the EcoRI and BamHI sites of pLox-hyg vector, and the GFP-IRES-tTRKRAB fragment from pLVCT-tTRKRAB (Addgene plasmid 11643) (Pankratz M T et al. Stem Cells 2007; 25:1511-1520) replaced hrGFP in CAG-hrGFP cassette, and then was inserted into the EcoRV site. The direction of the insertion was determined by restriction enzyme analysis.

Transfection of hESCs by Electroporation

Human ESC colonies were detached with dispase (1 mg/ml; Invitrogen) treatment for 3 min, washed with the ESC culture medium, and resuspended in 0.6 ml cold culture medium (1-2×10⁷ cells/one well of a 6-well plate). Linearized master vector DNA (30 ug in 0.1 ml of PBS) was mixed with ESCs using a 1-ml pipette tip. Cells were then exposed to a single pulse (320 V, 200 µF) using the BioRad Gene Pulser Xcell (0.4 cm gap cuvette; BioRad, Hercules, Calif.). The electroporated cells were incubated at room temperature for 5 min before they were plated and cultured under the regular hESC growth medium in three 6-well plates with MEF feeder layer. G418 selection (50 ug/ml, Invitrogen) was started 3 days after electroporation and the G418 concentration was increased to 100 ug/ml after one week. After two weeks, surviving colonies were picked out and expanded in each well of 24-well plates.

Flow Cytometry Analysis

ESCs were dissociated into single cells with trypsin-EDTA for 5 min. The cells were incubated with SSEA-4 antibody (mIgG3, Chemicon) or mIgG (as a negative control for SSEA-4 staining) for 45 min at 37° C., followed by washing with PBS three times and incubation with the secondary antibody Phycoerythrin (PE)-conjugated goat anti-mouse IgG (BD Bioscience). After washing the secondary antibody reaction, cell samples were analyzed using a FACScan flow cytometer (BD Bioscience). Dead cells were excluded from analysis by forward- and side-scatter gating. The mIgG stained cells were set up as a negative control for SSEA-4 analysis and the parental H9 cells were used as a negative control for GFP analysis. A minimum of 50,000 events was acquired for each sample. The data were analyzed with Cellquest software (BD Bioscience).

Quantification of Transgene Copy Numbers by Real-time PCR Analysis

The genomic DNA was extracted from every hESC clone by MasterPure™ DNA purification kit (Epicentre). Real-time PCR was performed using the Bio-Rad MyiQ real-time PCR detection system. The reaction was conducted under the following condition: template denaturation at 95° C. for 3 min, followed by 40 cycles of denaturation at 95° C. for 15 s, annealing at 55° C. for 30 s, and extension at 72° C. for 1 min. The primers were used for hrGFP: Forward CGGCTCT-GCTTCCCTTAGACT (SEQ ID NO:3); Reverse TCA-CAGCCAAGCATTCTACAAAC (SEQ ID NO:4), for GAPDH: Forward AACGTGTCAGTGGTGGACCTG (SEQ ID NO:5); Reverse AGTGGGTGTCGCTGTTGAAGT (SEQ ID NO:6). The PCR efficiency was examined with five dilutions of hESC genomic DNA and the specificity of individual gene primers was validated by the melting curve at the end of each PCR assay. To determine the integrating transgene copy number, the copy number of hrGFP gene was first determined as one gene copy by relating the CT value to the standard curve in the control cell line. The copy number of the hrGFP transgene in different cell clones was then compared with the control cell line and quantified by normalization against the reference GAPDH gene using the $2^{-\Delta\Delta CT}$ method.

Immunostaining and Microscopy

Immunohistochemical staining was performed according to Zhang et al [27]. Coverslip cultures were fixed in 4% paraformaldehyde in PBS for 15 min at room temperature. After washing with PBS, cells were incubated for 30 minutes in 10% normal goat serum to block non-specific antibody binding. They were then incubated for 1 hour in the primary antibody, washed in PBS and incubated for 1 hour in Alexa Fluor 488 goat anti-mouse IgG or Alexa Fluor 594 goat anti-rabbit IgG second antibodies (1:1000, Molecular Probes) and for 5 min in bisbenzamide (5 ng/ml; Hoechst No. 33342; Sigma). Coverslips were mounted in a mounting medium (Immunotech) and examined with a Nikon Eclipse E600 fluorescence microscope. The following primary antibodies were used: nestin (mIgG 1:200, Chemicon), Olig2 (rIgG 1:4000), βIII tubulin (TuJ1, mIgG 1:500, Sigma), GFAP (mIgG 1:500, Chemicon), HB9 (mIgG 1:50, DSHB), synapsin I (rIgG 1:1000, Calbiochem), Sox17 (mIgG 1:100, R&D), Pdx1 (rIgG 1:500, Abcam), Brachyury T (gIgG 1:50, R&D), cTnT (mIgG 1:500, Abcam). Quantification of HB9⁺ motoneuron was performed by averaging counts of fifteen neural cell aggregates from three independent experiments using Metamorph software (Universal Imaging Corporation).

Formation of Teratomas hESCs were injected subcutaneously into severe combined immunodeficient (SCID) mice (Jackson Laboratory, Bar Harbor, Me.) on the back. Two months after injection, mice were sacrificed and teratomas were removed. The teratomas were then postfixed with 4% paraformaldehyde in PBS, followed by cryoprotection in 30% sucrose overnight and cryosectioned to 25 µm. Histological examination of the sections was performed by hematoxylin and eosin staining. All animal experiments were performed following protocols approved by Institutional Animal Care and Use Committee.

Site-finding PCR

The transgene integration site was determined by site-finding PCR analysis (Tan G et al. Nucleic Acids Res. 2005; 33:e122). The site-finding PCR mixture included 2 µl of 10× long Taq DNA polymerase buffer, 2 µl of 10 mM dNTP solution, 0.5 U of long Taq DNA polymerase (Epicenter), 10 µmol of SiteFinder primer (5'-CAC GAC ACG CTA CTC AAC ACA CCA CCT CGC ACA GCG TCA TCA AGC GGC CGC NNN NNN GCC T-3' (SEQ ID NO:7)) and 100 ng of genomic DNA extracted from hESC samples. The final volume was brought to 20 µl with water, and then a single PCR cycle was run (Table 2). This was followed by two rounds of nested PCR (Table 1) using the following primers, respectively, SFP1 (5'-CAC GAC ACG CTA CTC AAC AC-3' (SEQ ID NO:8)), GSP1 (5'-TAT CCC GTA TTG ACG CCG GGC AAG-3' (SEQ ID NO:9)), SFP2 (5'-ACT CAA CAC ACC ACC TCG CAC AGC-3' (SEQ ID NO:10)), GSP2 (5'-AAG AGC AAC TCG GTC GCC GCA TAC-3' (SEQ ID NO:11)). SFP1 and SFP2 were nested primer from SiteFinder primer. GSP1 and GSP2 were designed from the backbone of the master vector. The products were separated on 1.0% agarose gels. The PCR products were isolated and cloned into the pBluescript SK vector between the restriction sites of NotI and EcoRV. The positive clones were selected for sequencing. DNA sequence analyses were carried out using the BLAST program in the human genome sequence.

Purification of TAT-Cre Protein

TAT-Cre fusion proteins were expressed from the plasmid pTAT-Cre (gift from Prof. Dowdy). (Wadia J S et al. Nat. Med. 2004; 10:310-315.) The proteins were expressed in *E. coli* strain BL21 (DE3). Bacterial cultures (1 L), grown to an A600 of 0.6-1.0, and induced with 0.5 mM IPTG. After harvesting, the bacterial cells were lysed in 50 ml Ni-NTA lysis buffer (50 mM sodium phosphate and 300 mM NaCl, pH 8.0) containing 50 ul Benzonase and centrifuged. The clear lysate was incubated with Ni-NTA His.Bind Resins (Novagen) for 1 hr and packed into a gravity-flow column. After affinity chromatography, recombinant proteins were eluted and dialyzed in PBS supplemented with 0.3 M NaCl and 8% glycerol. The protein concentration was determined with BCA reagent (Pierce).

Cre RMCE with the Targeting Vector

The hESCs were dissociated with dispase and split 1:3 in the 6-well plate (3×10⁶ cells/well). After culturing for 24 hrs, the ESC medium was replaced with fresh medium. Targeting vector DNA (2 ug) and Fugene®HD reagent (6 ul) were mixed in 100-ul OPTIMEM (Invitrogen) for 15 min and then applied directly into the cell culture. Five hrs later, 2 uM of TAT-Cre protein was added in the culture. The cells were fed with fresh ESC medium the next day and cultured for additional three days before hygromycin B (25 ug/ml) was added to select antibiotics-resistant colonies for two weeks. The surviving colonies were picked out and expanded in 24-well plates. The correct exchanged cell clones were identified by PCR.

Southern Blot Analysis 20 ug genomic DNA was extracted and digested with BamHI, then run in 0.8% agarose gels and blotted onto the nylon membrane (Pierce). $^{32}$P-CTP labeled CAG promoter probe was used to detect the integration of the targeting vector.

Example 2

Identification of Insertion Sites

Site-finding PCR

The transgene integration site was determined by site-finding PCR analysis. Tan G, Gao Y, Shi M et al. Nucleic Acids Res. 2005; 33:e122. The site-finding PCR mixture included 2 µl of 10× long Taq DNA polymerase buffer, 2 µl of 10 mM dNTP solution, 0.5 U of long Taq DNA polymerase (Epicenter), 10 µmol of SiteFinder primer (5'-CAC GAC ACG CTA CTC AAC ACA CCA CCT CGC ACA GCG TCA TCA AGC GGC CGC NNN NNN GCC T-3' (SEQ ID NO:7)) and 100 ng of genomic DNA extracted from hESC samples. The final volume was brought to 20 µl with water, and then a single PCR cycle was run. This was followed by two rounds of nested PCR using the following primers, respectively, SFP1 (5'-CAC GAC ACG CTA CTC AAC AC-3' (SEQ ID NO:8)), GSP1 (5'-TAT CCC GTA TTG ACG CCG GGC AAG-3' (SEQ ID NO:9)), SFP2 (5'-ACT CAA CAC ACC ACC TCG CAC AGC-3' (SEQ ID NO:10)), GSP2 (5'-AAG AGC AAC TCG GTC GCC GCA TAC-3' (SEQ ID NO:11)). SFP1 and SFP2 were nested primer from SiteFinder primer. GSP1 and GSP2 were designed from the backbone of the master vector. The products were separated on 1.0% agarose gels. The PCR products were isolated and cloned into the pBluescript SK vector between the restriction sites of NotI and EcoRV. The positive clones were selected for sequencing. DNA sequence analyses were carried out using the BLAST program in the human genome sequence.

Results

Following are the two insertion sites we identified:

Insertion Site one: On chromosome 4q12, 34 kb from IGFBP7 gene and 30 kb from LOC255130 gene, the genomic nucleotide sequence immediately upstream of the inserted transgene is:

(SEQ ID NO:1)
TGCAATCTCCGCCTCCGGACTCAGGTGATTCTCCCACCTC.

Insertion Site two: On chromosome 7q11.23, 22.5 kb from CLDN3 gene and 40 kb from CLDN4 gene, the genomic nucleotide sequence immediately upstream of the inserted transgene is:

(SEQ ID NO:2)
ACATAGGCATGATTGATTGCATCACTGGCCAATGGCAATC.

TABLE 1

Efficiency of GFP expression in the transfected human and mouse ESCs

| | GFP positive clones/total clones | | | | |
|---|---|---|---|---|---|
| | Human ESC | | | | |
| Promoter | Exp 1 | Exp 2 | Exp 3 | Total | Mouse ESC |
| CAG | 6/35 | 4/25 | 7/38 | 17/98 (17.3%) | 211/254 (83.1%) |

TABLE 2

Determine the integration copy number by qPCR

| hESC clone | $C_T$-hrGFP | $C_T$-GAPDH | $C_T$-hrGFP – $C_T$-GAPDH | $\Delta\Delta C_T$ | $2^{-\Delta\Delta C_T}$ (copy number) |
|---|---|---|---|---|---|
| Control* | 22.44 | 19.02 | 3.42 | 0 | 1 (1) |
| A1 | 23.81 | 21.32 | 2.49 | −0.93 | 1.91 (2) |
| A2 | 22.31 | 18.68 | 3.63 | 0.21 | 0.86 (1) |
| A3 | 22.57 | 19.05 | 3.52 | 0.1 | 0.93 (1) |
| A4 | 22.0 | 18.73 | 3.27 | −0.15 | 1.11 (1) |
| A5 | 22.09 | 19.69 | 2.4 | −1.02 | 2.03 (2) |
| A6 | 21.75 | 18.82 | 2.93 | −0.49 | 1.40 |
| A7 | 22.26 | 19.80 | 2.46 | −0.96 | 1.95 (2) |
| A8 | 22.64 | 19.01 | 3.6 | 0.18 | 0.88 (1) |
| A9 | 23.15 | 19.81 | 3.34 | −0.08 | 1.05 (1) |
| B1 | 21.58 | 19.65 | 1.93 | −1.16 | 2.23 (2) |
| B2 | 21.97 | 19.05 | 2.92 | −0.17 | 1.12 (1) |
| B3 | 21.50 | 19.28 | 2.22 | −0.87 | 1.83 (2) |
| B4 | 22.0 | 18.73 | 3.27 | 0.18 | 0.88 (1) |
| B5 | 21.11 | 19.04 | 2.07 | −1.02 | 2.03 (2) |
| B6 | 21.09 | 18.96 | 2.13 | −0.96 | 1.95 (2) |
| B7 | 22.27 | 18.97 | 3.30 | 0.21 | 0.86 (1) |
| B8 | 21.55 | 19.35 | 2.2 | −0.89 | 1.85 (2) |

*One hESC clone was determined to have one integration hGFP copy by absolute quantification with a standard curve.

We claim:

1. A method of creating a human pluripotent transgenic stem cell line comprising the steps of
   a. selecting a pluripotent stem cell line, and
   b. inserting heterologous DNA at an insertion site selected from the group consisting of insertion site one and insertion site two to form a transgenic cell line, wherein the insertion site one is immediately downstream of SEQ ID NO:1 on chromosome 4q12, 34 kb from IGFBP7 gene and 30 kb from LOC255130 gene, and wherein the insertion site two is immediately downstream of SEQ ID NO:2 on chromosome 7q11.23, 22.5 kb from CLDN3 gene and 40 kb from CLDN4 gene.

2. The method of claim 1, wherein the heterologous DNA is an exchange cassette and the transgenic cell line formed is a master cell line.

3. The method of claim 1, wherein the heterologous DNA is a transgene.

4. The method of claim 3, wherein the transgene is driven by a promoter.

5. The method of claim 4, wherein the promoter is an inducible promoter.

6. The method of claim 4, wherein the promoter is a cell type specific promoter.

7. The method of claim 2, wherein the exchange cassette is a loxP exchange cassette.

8. The method of claim 7, wherein the loxP exchange cassette comprises a double loxP sequence, a marker gene driven by a promoter and a selection gene.

9. The method of claim 8, wherein the promoter is an inducible promoter.

10. The method of claim 8, wherein the promoter is a cell type specific promoter.

11. The method of claim 1, wherein the insertion site is insertion site one.

12. The method of claim 1, wherein the insertion site is insertion site two.

13. A method of creating a cell line comprising a transgene of interest, comprising the steps of
   a. exposing the master cell line of claim 2 to a vector comprising a second exchange cassette, wherein the second exchange cassette comprises a transgene of interest driven by a promoter, and
   b. selecting cells, wherein the transgene of interest has integrated into the cell.

14. The method of claim 13, wherein the exchange cassette is a loxP exchange cassette and the exposure of master cell line to a vector is in the presence of ere recombinase.

15. The method of claim 14, wherein the loxP exchange cassette is a double loxP exchange cassette.

16. The method of claim 13, wherein the promoter is an inducible promoter.

17. The method of claim 13, wherein the promoter is a cell type specific promoter.

18. A population of pluripotent stem cells comprising heterologous DNA integrated at an insertion site selected from the group consisting of insertion site one and insertion site two, wherein the insertion site one is immediately downstream of SEQ ID NO:1 on chromosome 4q12, 34 kb from IGFBP7 gene and 30 kb from LOC255130 gene, and wherein the insertion site two is immediately downstream of SEQ ID NO:2 on chromosome 7q11.23, 22.5 kb from CLDN3 gene and 40 kb from CLDN4 gene.

19. The population of claim 18, wherein the insertion site is insertion site one.

20. The population of claim 18, wherein the insertion site is insertion site two.

21. A population of pluripotent stem cells comprising an exchange cassette integrated at an insertion site selected from the group consisting of insertion site one and insertion site two, wherein the insertion site one is immediately downstream of SEQ ID NO:1 on chromosome 4q12, 34 kb from IGFBP7 gene and 30 kb from LOC255130 gene, and wherein the insertion site two is immediately downstream of SEQ ID NO:2 on chromosome 7q11.23, 22.5 kb from CLDN3 gene and 40 kb from CLDN4 gene.

22. The population of claim 21, wherein the insertion site is insertion site one.

23. The population of claim 21, wherein the insertion site is insertion site two.

24. The population of claim 21 wherein the exchange cassette is a loxP exchange cassette.

25. The population of claim 24, wherein the loxP exchange cassette is a double loxP exchange cassette.

* * * * *

UNITED STATES PATENT AND TRADEMARK OFFICE
CERTIFICATE OF CORRECTION

PATENT NO. : 7,947,501 B2
APPLICATION NO. : 12/322809
DATED : May 24, 2011
INVENTOR(S) : Zhang et al.

It is certified that error appears in the above-identified patent and that said Letters Patent is hereby corrected as shown below:

Column 1, line 63 "(MV2)" should be -- AAV2) --

Column 3, line 57 "(I)" should be -- (H) --

Column 3, line 58 "(J)" should be -- (I) --

Column 3, line 63 "(K, L)" should be -- (J, K) --

Column 10, line 25 "2L" should be -- 2I --

Column 12, line 28 "2ul" should be -- 2, 1 --

Column 14, line 6 "Fomi" should be -- Forni --

Column 16, line 28 "umol" should be -- pmol --

Column 17, line 28 "umol" should be -- pmol --

Signed and Sealed this
Twelfth Day of July, 2011

David J. Kappos
*Director of the United States Patent and Trademark Office*